(12) United States Patent
Cerutti et al.

(10) Patent No.: US 8,828,394 B2
(45) Date of Patent: Sep. 9, 2014

(54) METHODS FOR TREATING IGE-MEDIATED DISORDER

(75) Inventors: Andrea Cerutti, Forest Hills, NY (US); Kang Chen, Nanjing (CN)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/260,008

(22) PCT Filed: Apr. 1, 2010

(86) PCT No.: PCT/US2010/029541
§ 371 (c)(1),
(2), (4) Date: Sep. 23, 2011

(87) PCT Pub. No.: WO2010/120566
PCT Pub. Date: Oct. 21, 2010

(65) Prior Publication Data
US 2012/0020979 A1    Jan. 26, 2012

Related U.S. Application Data

(60) Provisional application No. 61/165,619, filed on Apr. 1, 2009.

(51) Int. Cl.
*A61K 39/395* (2006.01)
*A61K 38/16* (2006.01)
*C07K 16/42* (2006.01)

(52) U.S. Cl.
CPC ............ *A61K 38/16* (2013.01); *C07K 16/4283* (2013.01); *C07K 2317/75* (2013.01); *A61K 39/39566* (2013.01); *C07K 2317/24* (2013.01); *Y10S 424/805* (2013.01); *Y10S 424/81* (2013.01); *Y10S 530/862* (2013.01); *Y10S 530/868* (2013.01)

USPC ................. 424/144.1; 424/133.1; 424/141.1; 424/153.1; 424/805; 424/810; 530/862; 530/388.22; 530/388.73; 530/389.6; 530/868; 514/1.7

(58) Field of Classification Search
None
See application file for complete search history.

(56) References Cited

U.S. PATENT DOCUMENTS 4,921,667 A * 5/1990 Coico et al. .................. 424/85.2
5,530,101 A * 6/1996 Queen et al. ............... 530/387.3

OTHER PUBLICATIONS

Goroff et al., J Immunol. Apr. 1, 1986;136(7):2382-92.*
Kerr et al., J Immunol. May 15, 1991;146(10):3314-21.*
Campbell, A., Monoclonal Antibody Technology, 1984, Elsevier Science Publishers B.V., pp. 1-32.*
Janeway et al., Immunobiology, $5^{th}$ edition, 2001, Garland Science, 12-5 to 12-14, 8 pages.*
Janeway et al., Immunobiology, 5th edition, 2001, Garland Science, Figure 12.18, one page.*
Pecanha et al., J Immunol. Mar. 15, 1993;150(6):2160-8.*
Yoshimoto et al., Science. Dec. 15, 1995;270(5243):1845-7.*
Seder et al., Proc Natl Acad Sci U S A. Apr. 1, 1991;88(7):2835-9.*
Conrad et al., J Exp Med. May 1, 1990;171(5):1497-508.*

* cited by examiner

*Primary Examiner* — Michael Szperka
(74) *Attorney, Agent, or Firm* — Scully, Scott, Murphy & Presser, P.C.

(57) ABSTRACT

This invention relates to methods of treating IgE mediated disorders such as allergy and asthma based on activating surface-bound IgD molecules on basophils. The invention also relates to methods of making IgD, as well as methods of screening for antimicrobial agents from IgD-activated basophils.

8 Claims, 19 Drawing Sheets

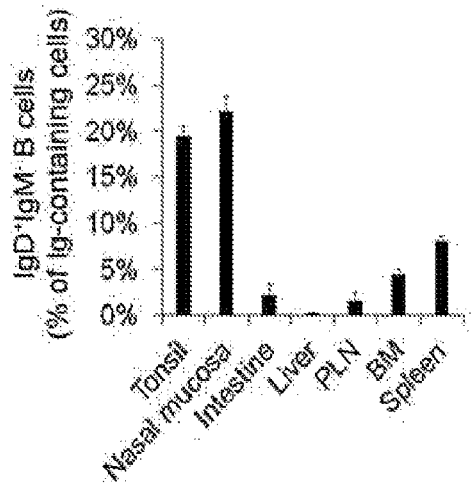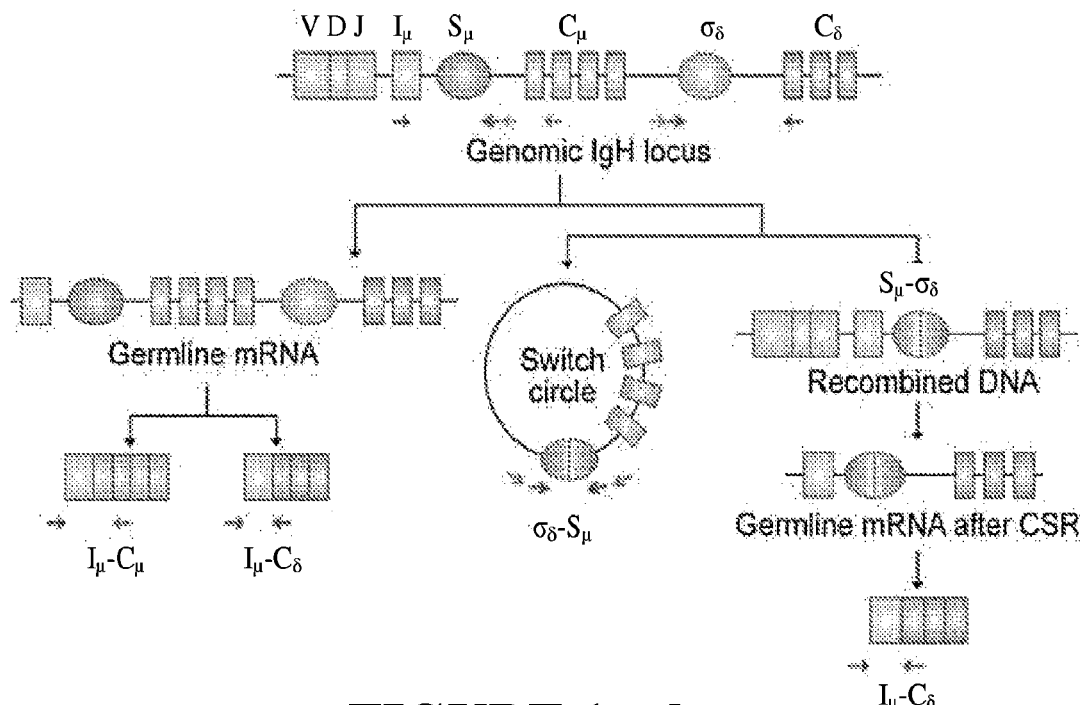
FIGURE 1 a-b

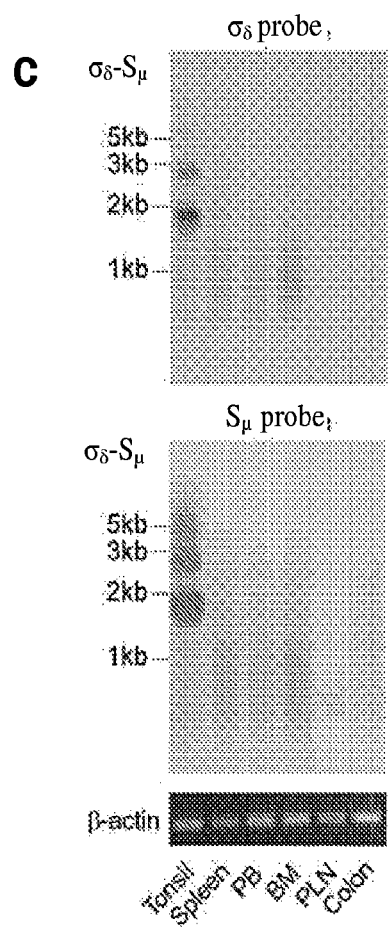
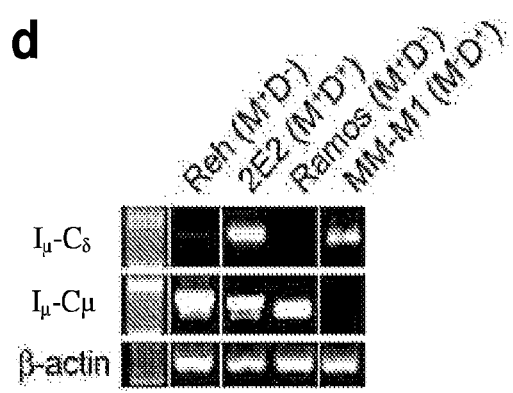
FIGURE 1 c-d

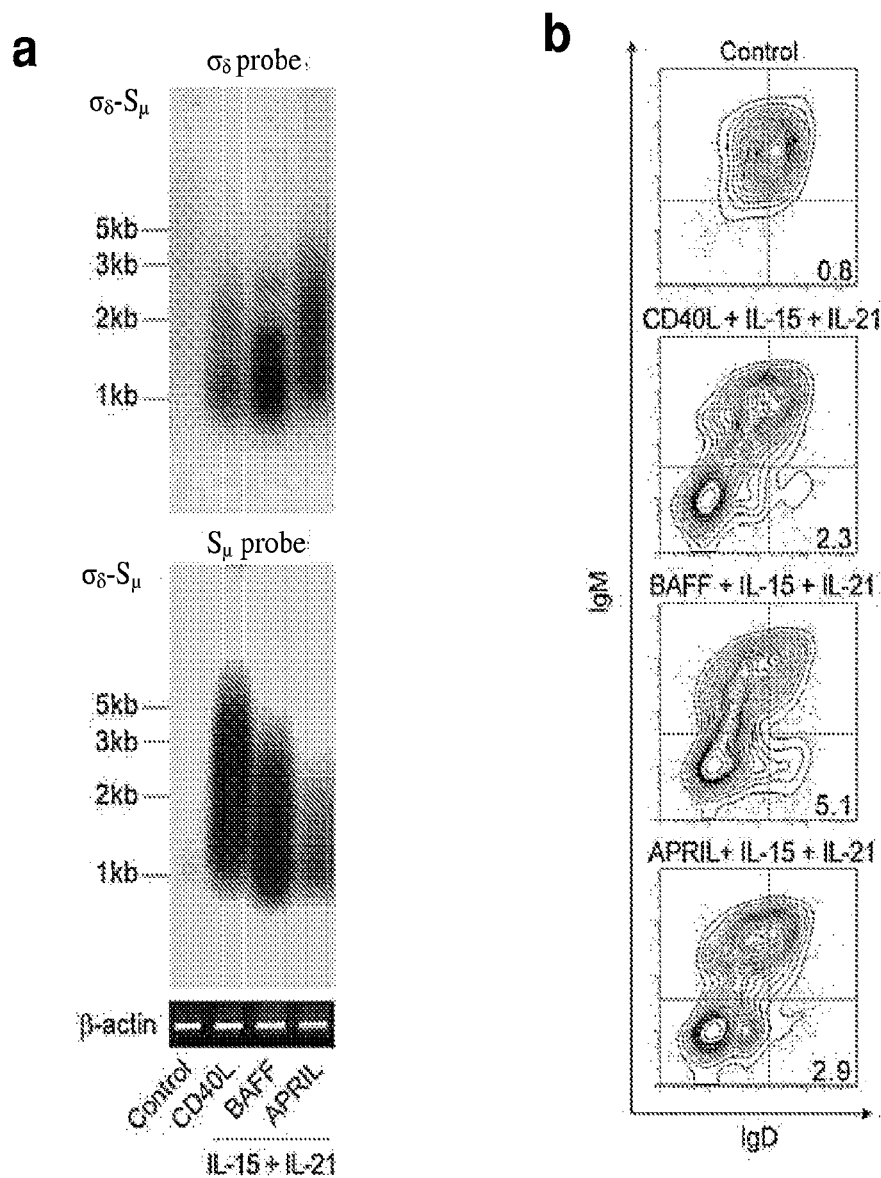
FIGURE 2 a-b

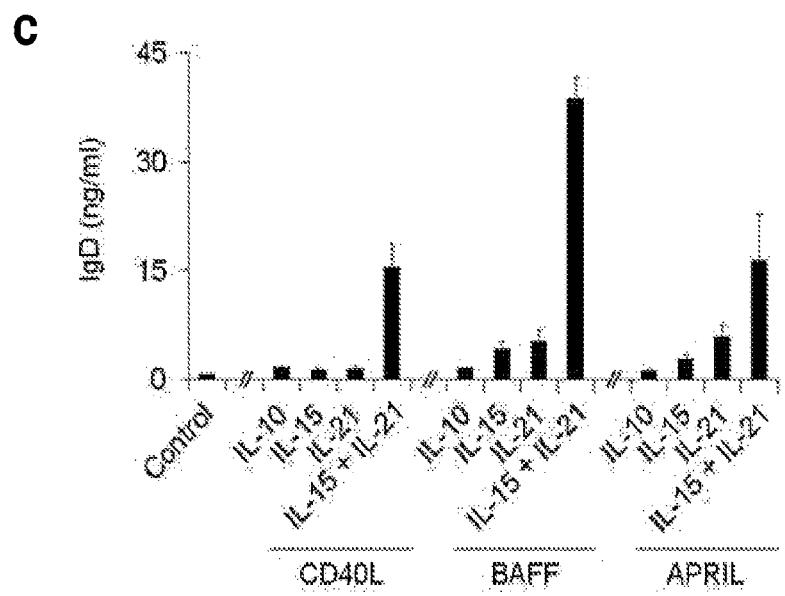
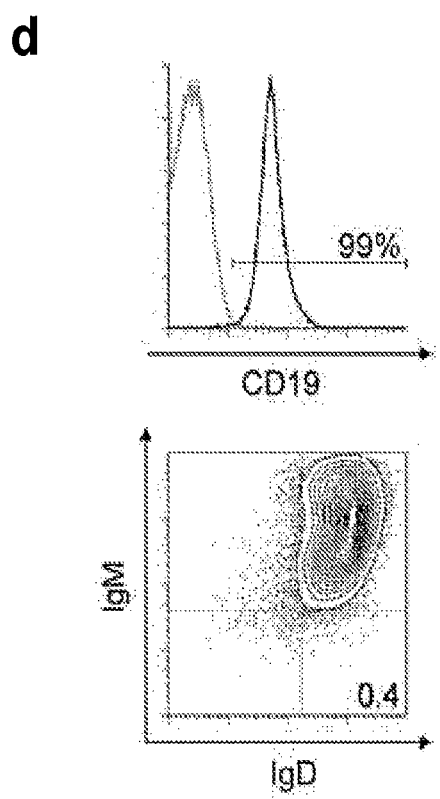
FIGURE 2 c-d

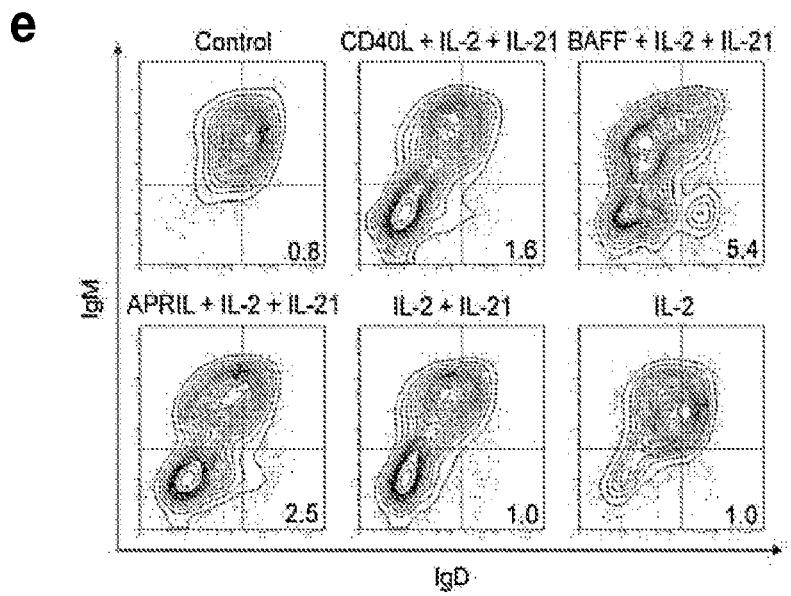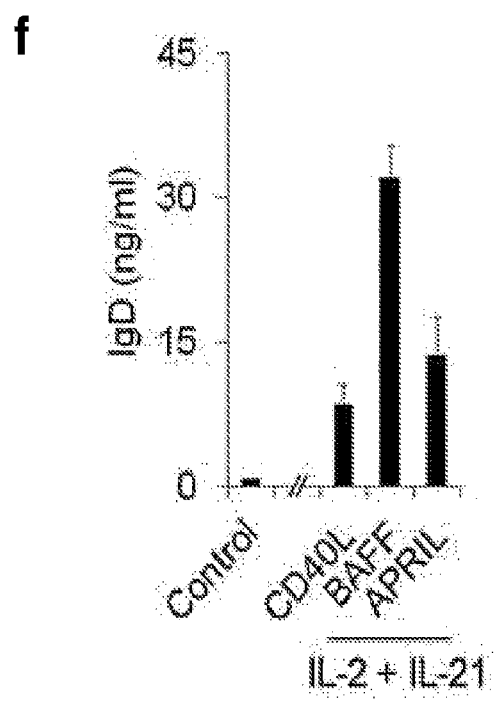
FIGURE 2 e-f

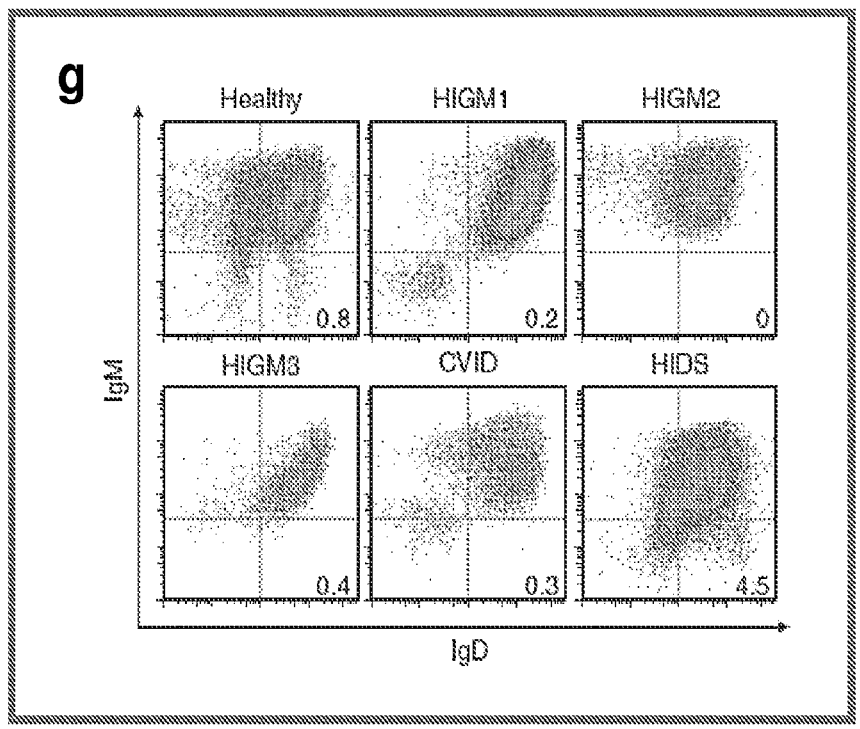
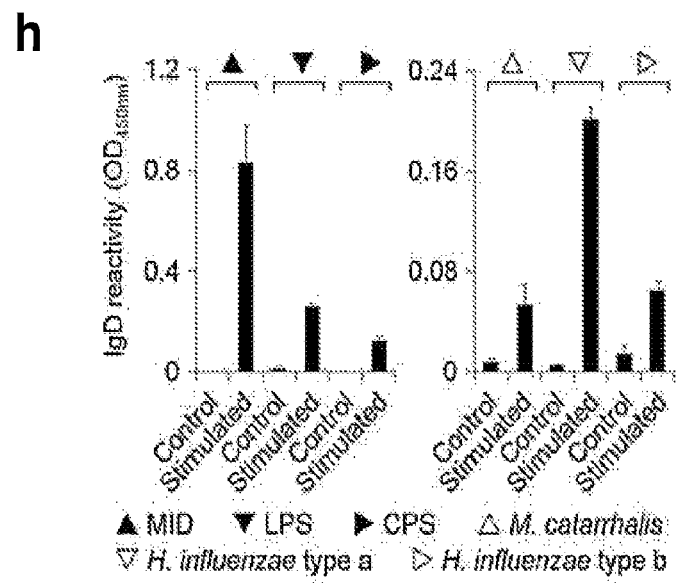
FIGURE 2 g-h

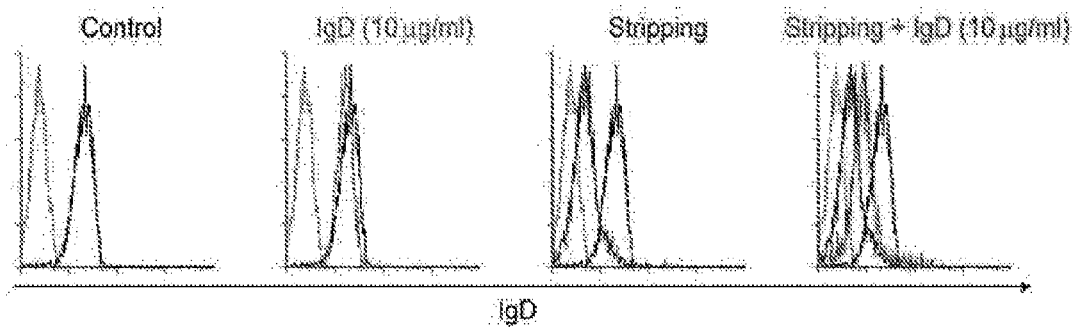
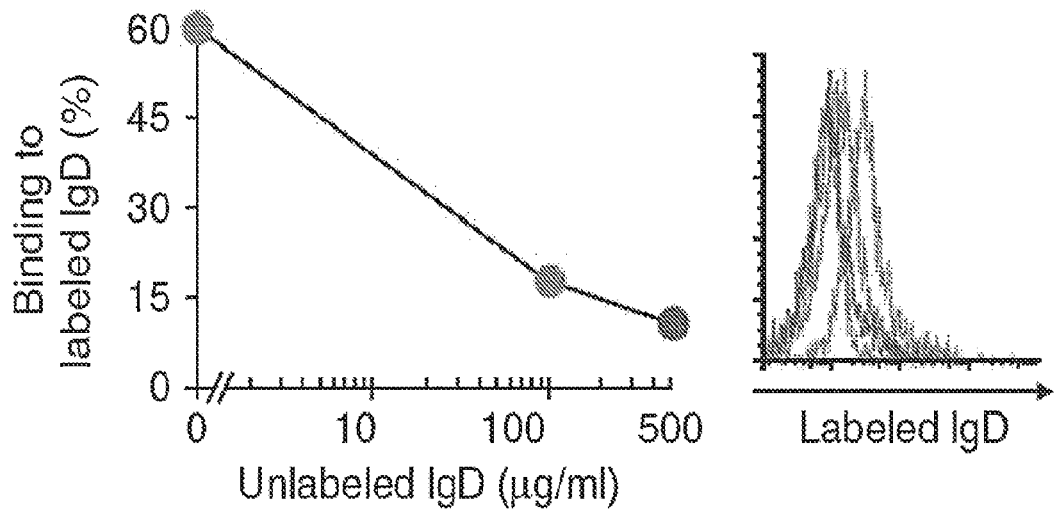
FIGURE 3 b-c

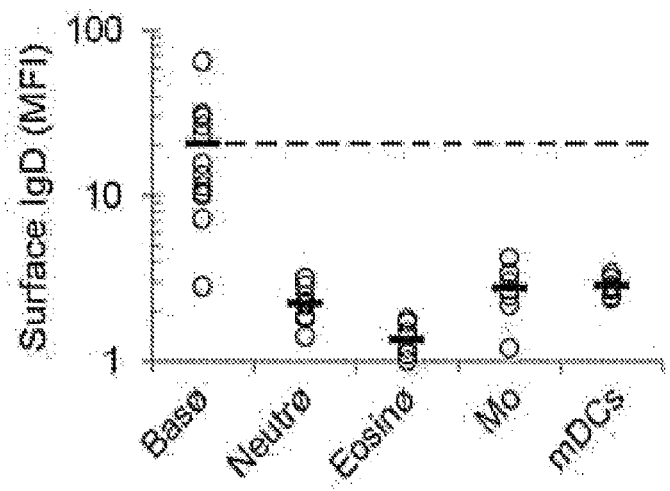
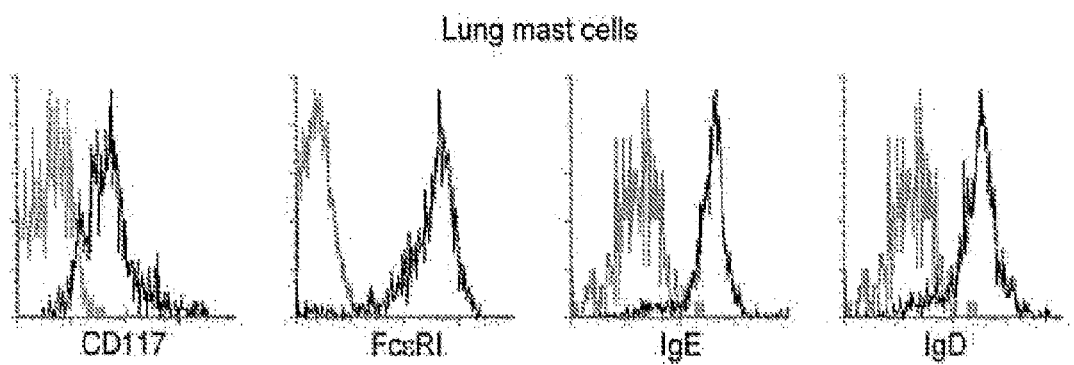
FIGURE 3 d-e

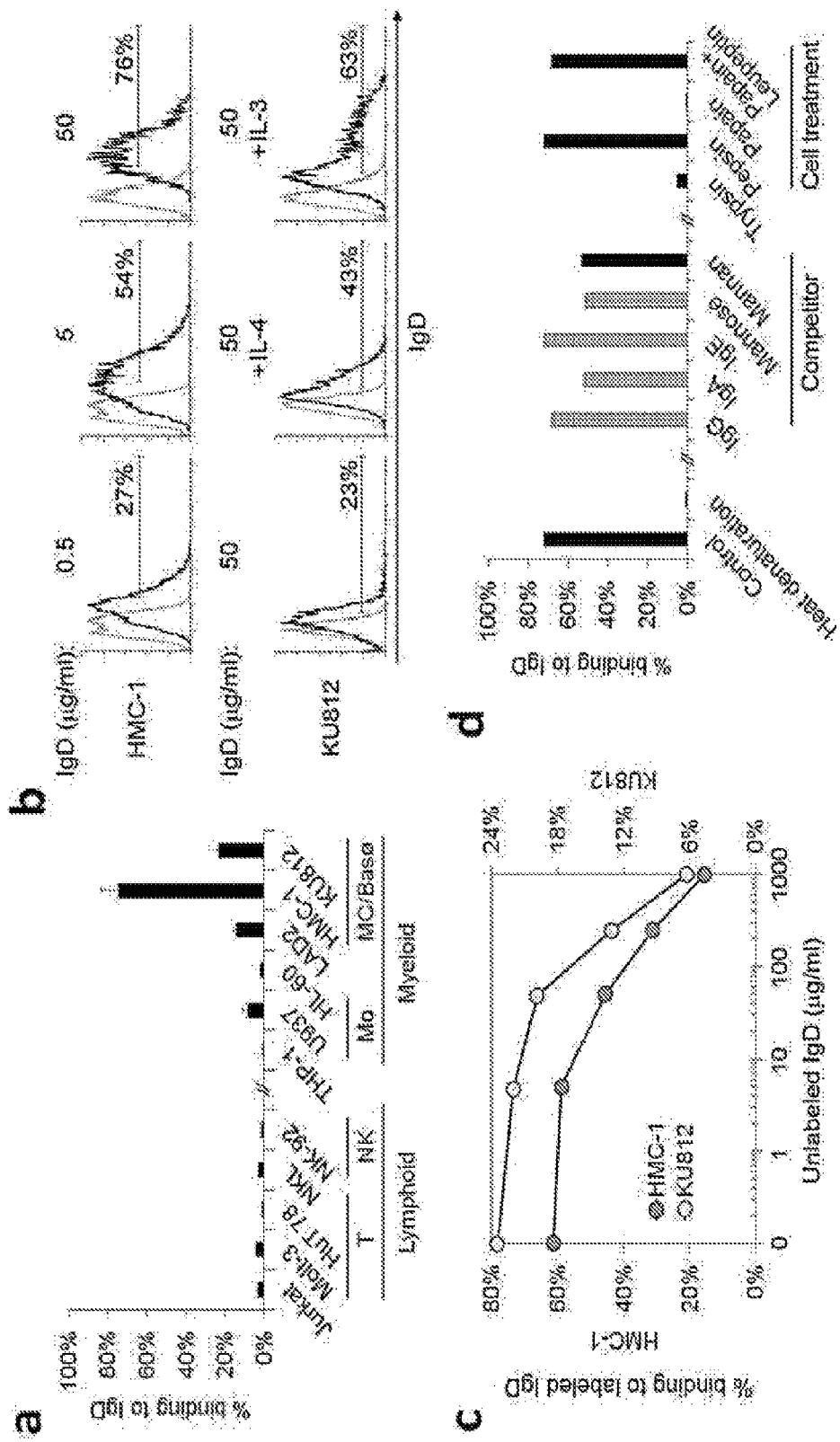
FIGURE 4 a-d

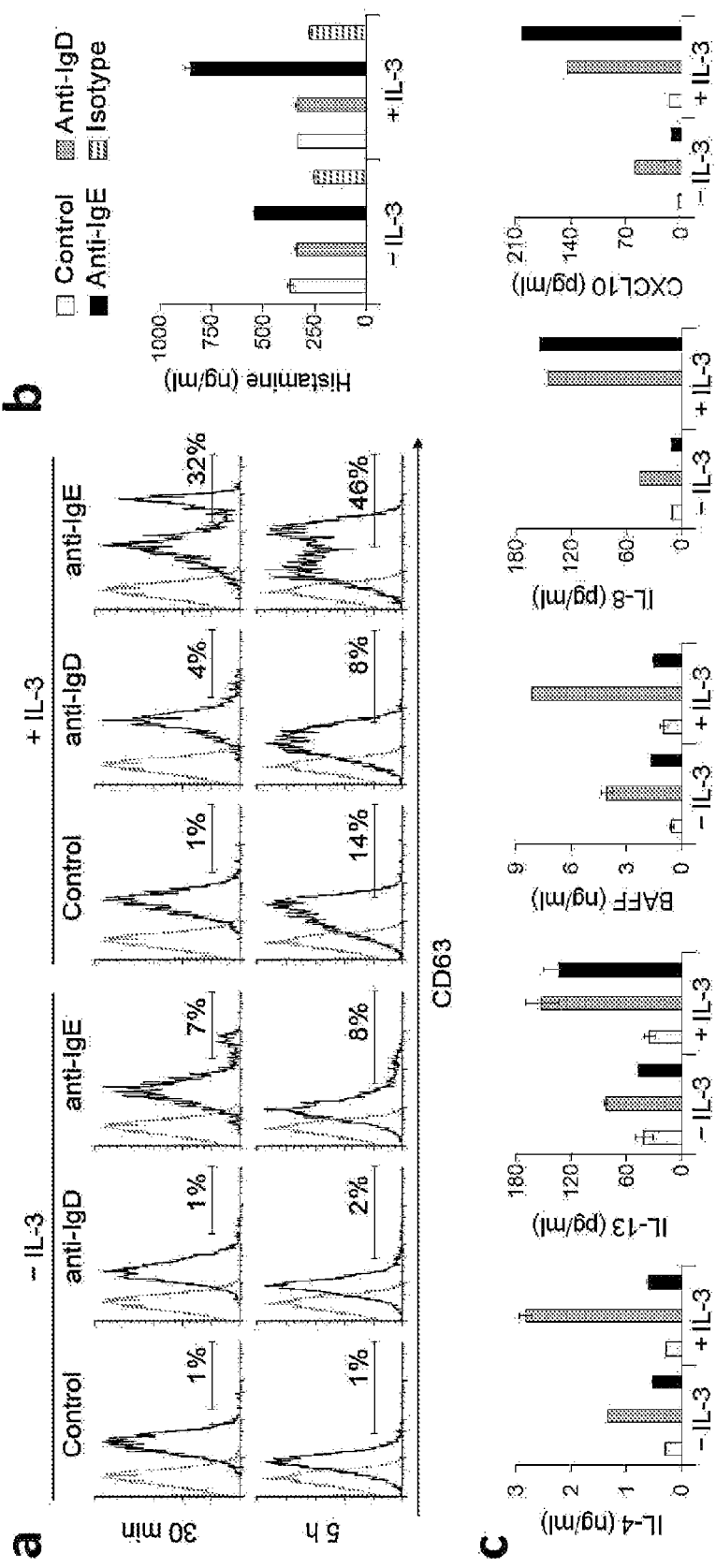
FIGURE 5 a-c

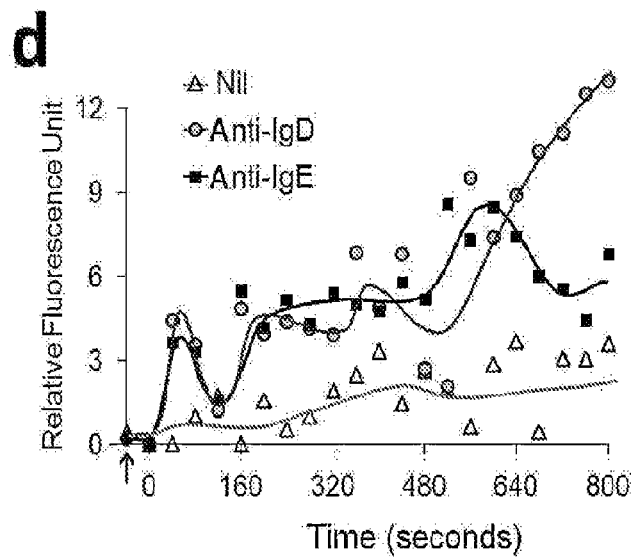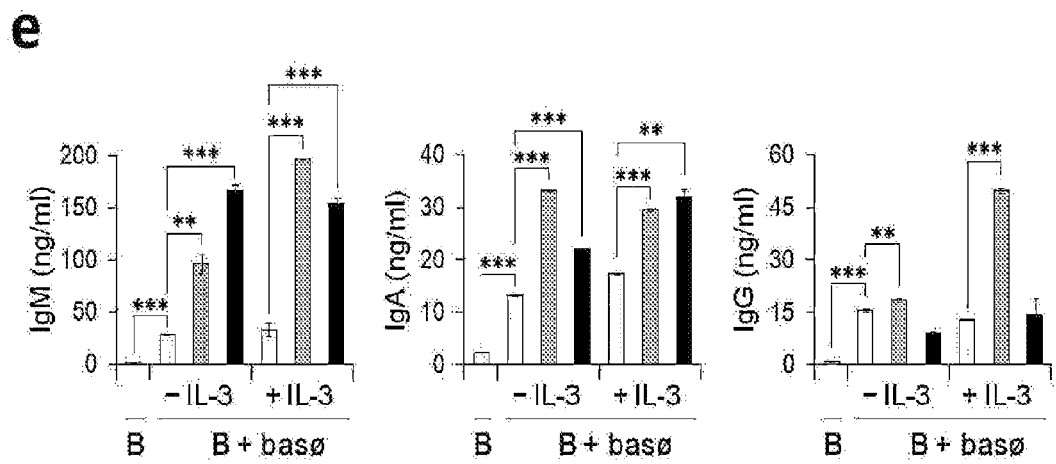
FIGURE 5 d-e

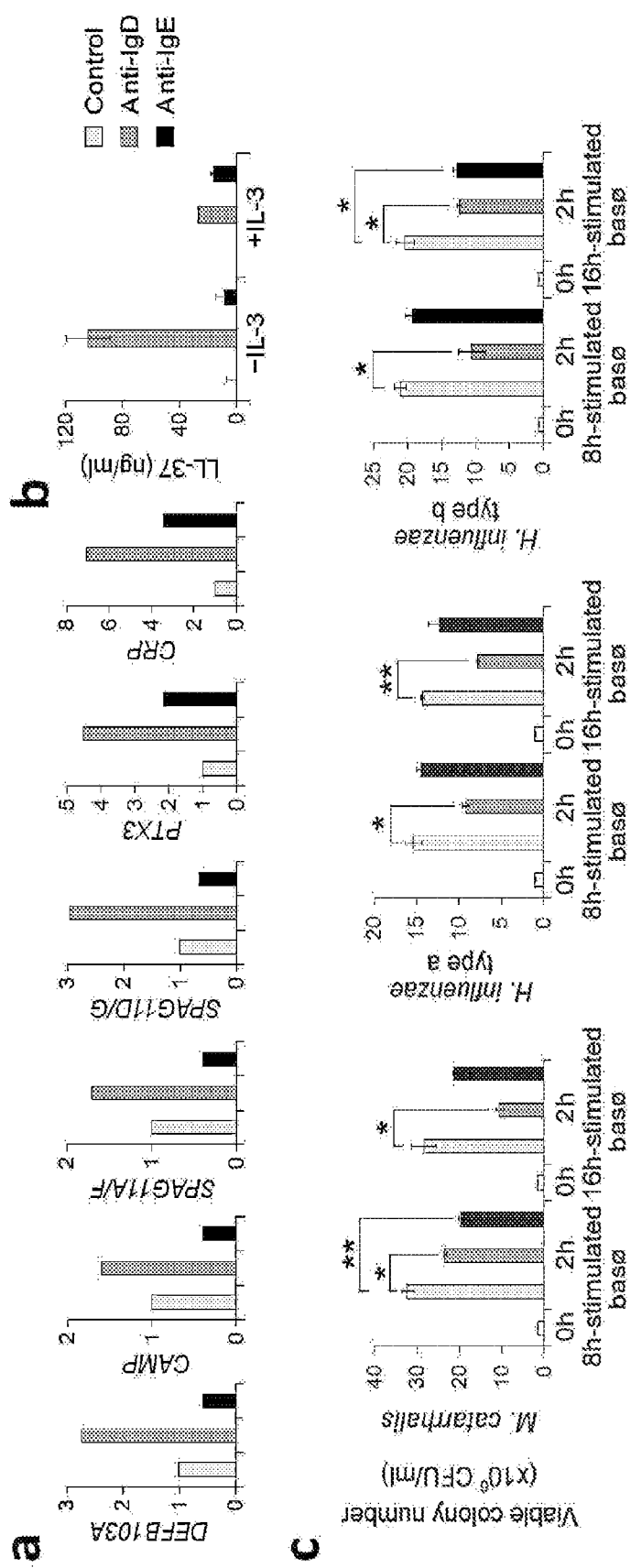
FIGURE 6 a-c

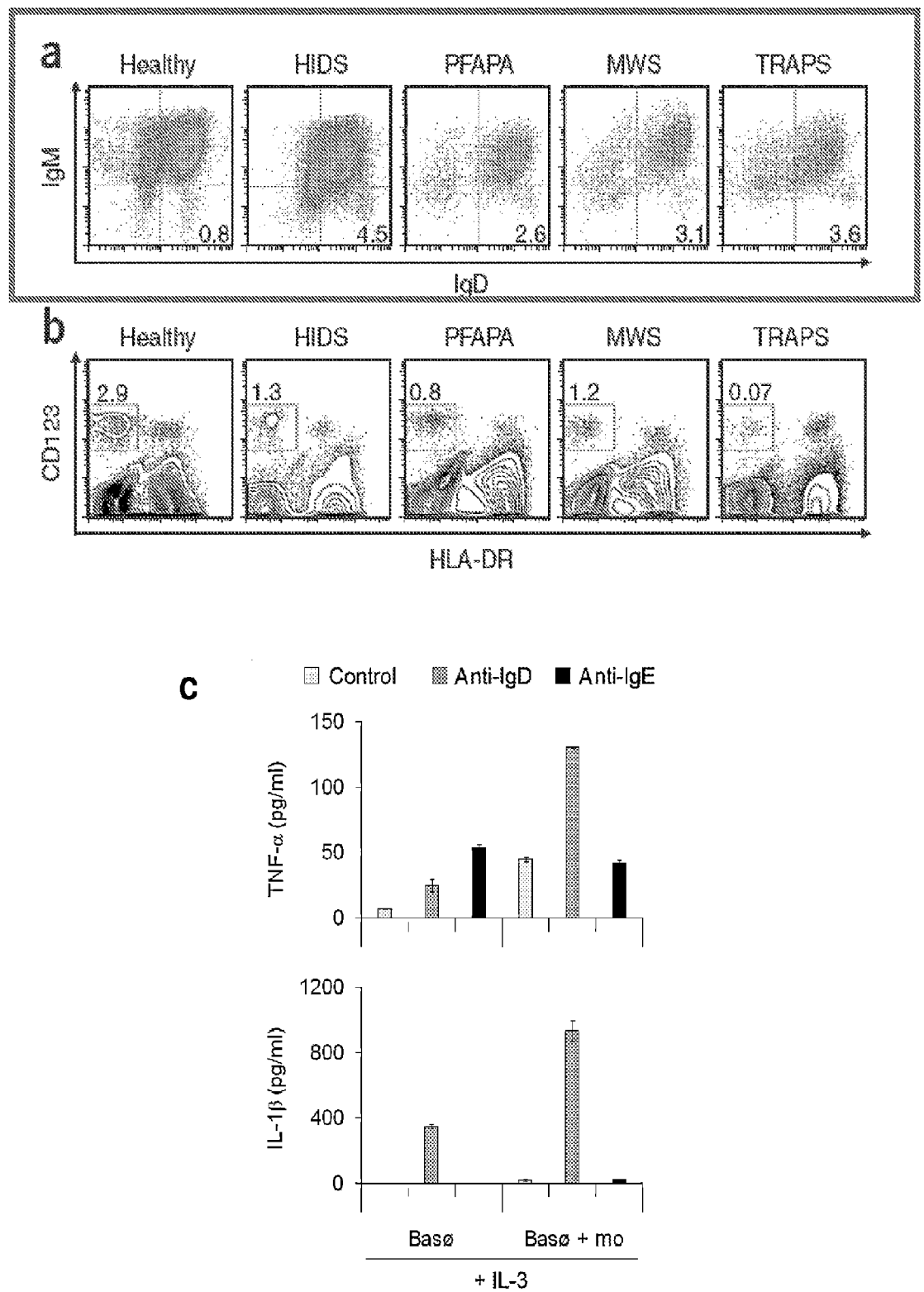
FIGURE 7 a-c b

```
  1  000+00-000 00000+00+- 0000000000 0000000000 0000000000 0+000-00++
 61  -000000000 0000000+00 -0+0000000 0+0++-00+0 0-00+00000 00000000-0
121  000+000000 00+000+00- -+++-+-+-- 0--+-0+00- 0000000000 00000000-0
181  00+-+00000 00000-0+-0 0000-000+0 00000--000 -+00000000 00+0000+00
241  0000000000 000000000+ 0000+-0000 000+000000 000-00-000 0000-00000
301  000000000- -0+-000000 000+000000 0000000000 +000000000 000000000-
361  -0+000000+ 00-00000-0 000+
```

Positive charge clusters (cmin =  9/30 or 12/45 or 15/60):  none
Negative charge clusters (cmin =  9/30 or 12/45 or 14/60):  none
Mixed charge clusters (cmin = 14/30 or 19/45 or 24/60):
   From  142 to  161:    KKKKEKEKEEQEERETKTPEC (SEQ ID NO:1)
                         +++-+-+--0--+-0+00-0
   quartile: 2; size: 20, +count:  7, -count:  8, 0count:  5;
   t-value: 10.34 *
   K:  6 (30.0%);  E:  8 (40.0%);  T:  2 (10.0%);

c

```
IgD:                    ---EKKKE-KEKEEQEERETKTPEC---(SEQ ID NO:2)
                           XBBBX-BX (SEQ ID NO:3)
                           ||||| ||
Heparin α-helical ligand:  XBBBXXBX (SEQ ID NO:4)
```

METHODS FOR TREATING IGE-MEDIATED DISORDER

CROSS-REFERENCE TO RELATED APPLICATION

This application claims the benefit of priority from U.S. Provisional Application No. 61/165,619, filed on Apr. 1, 2009.

STATEMENT REGARDING FEDERALLY SPONSORED RESEARCH OR DEVELOPMENT

This invention was made with support from the National Institutes of Health under grants R01 AI057653, R01AI057653 supplement, R01AI074378 and T32 AI07621.

FIELD OF THE INVENTION

This invention relates to methods of treating IgE mediated disorders such as allergy and asthma based on activating surface-bound IgD molecules on basophils. The invention also relates to methods of making IgD, as well as methods of screening for antimicrobial agents from IgD-activated basophils.

BACKGROUND OF THE INVENTION

Recent studies demonstrate that IgD was present in the ancestor of all jawed vertebrates and arose together with IgM at the time of the emergence of the adaptive immune system, approximately 500 million years ago. While IgM remains stable over evolutionary time, IgD shows greater structural plasticity and can be predominantly expressed as a transmembrane or secretory molecule in a species-specific manner.

IgM and IgD are the first antibody isotypes expressed during B cell ontogeny. Bone marrow B cell precursors acquire surface IgM after assembling heavy (H) and light (L) chain variable region exons from prototypic variable (V), diversity (D) and joining (J) gene segments through an antigen-independent process mediated by recombination activating gene (RAG)-1 and RAG-2 proteins. After leaving the bone marrow to colonize secondary lymphoid organs, 13 cells acquire surface IgD of the same specificity as surface IgM through alternative splicing of a pre-messenger RNA comprising VDJ and both heavy chain constant μ ($C_\mu$) and $C_\delta$ exons (Maki et al., *Cell* 24: 353-365, 1981). The significance of dual IgM and IgD expression remains unclear, because either isotype largely compensates for the loss of the other (Nitschke et al., *Proc. Natl. Acad. Sci. USA* 90: 1887-1891, 1993; Roes et al., *J. Exp. Med.* 177: 45-55, 1993; Lutz et al., *Nature* 393: 797-801, 1998).

After encountering antigen in secondary lymphoid organs, mature B cells transcriptionally down-regulate surface IgD (Monroe et al., *Eur. J. Immunol.* 13: 208-213, 1983) and thereafter undergo somatic hypermutation (SHM) and class switch DNA recombination (CSR), two Ig gene-diversifying processes that require the DNA-editing enzyme activation-induced cytidine deaminase (AID) (Muramatsu et al., *Cell* 102: 553-563, 2000). SHM introduces point mutations into $V_H DJ_H$ and $V_L J_L$ exons, thereby providing the structural correlate for selection of high-affinity Ig variants by antigen (Odegard et al., *Nat. Rev. Immunol.* 6: 573-583, 2006), whereas CSR substitutes the $C_\mu$ gene with $C_\gamma$, $C_\alpha$ or $C_\epsilon$, thereby generating secondary IgG, IgA and IgE isotypes with the same antigen binding specificity as IgM but additional effector functions (Chaudhuri et al., Nat. Rev. Immunol. 4: 541-552, 2004). Ultimately, antigen-experienced B cells generate antibody-secreting plasma cells and memory B cells (McHeyzer-Williams et al., *Curr. Opin. Immunol.* 11: 172-179, 1999). These latter cells form new plasma cells upon exposure to previously encountered antigens. In general, plasma cell-derived IgG, IgA and IgE antibodies facilitate the elimination of invading pathogens by activating powerful Fc receptors that enhance the phagocytic, cytotoxic and pro-inflammatory functions of various innate immune cells, including granulocytes (Stavnezer et al., *Adv. Immunol.* 61: 79-146, 1996).

Instead of switching from IgM to IgG, IgA or IgE, some B cells switch to IgD (Arpin et al., *J. Exp. Med.* 187: 1169-1178, 1998) The resulting $IgD^+ IgM^-$ plasma cells release highly mutated mono- and polyreactive IgD antibodies mostly containing λ IgL chains in the blood as well as respiratory, salivary, lacrimal and mammary secretions (Rowe et al., *J. Exp. Med.* 121: 171-199, 1965; Preudthomme et al., *Mol. Immunol.* 37: 871-887, 2000; Plebani et al., *Clin. Exp. Immunol.* 53: 689-696, 1983; Liu et al., *Immunity* 4: 603-613, 1996; Brandtzaeg et al., *Immunol. Rev.* 171: 45-87, 1999; Koelsch et al., *J. Clin. Invest.* 117: 1558-1565, 2007). IgD-deficient mice have fewer B cells, delayed affinity maturation, and weaker production of IgG1 and IgE, two isotypes dependent on the cytokine interleukin-4 (IL-4) (Nitschke et al., *Proc. Natl. Acad. Sci. USA* 90: 1887-1891, 1993; Roes et al., *J. Exp. Med.* 177: 45-55, 1993) Conversely, mice injected with anti-IgD antibodies produce more IgG1 and IgE and show robust IL-4 production by T cells and basophils (Conrad et al., *J. Exp. Med.* 171: 1497-1508, 1990; Seder et al., *Proc. Natl. Acad. Sci. USA*, 88: 2835-2839, 1991; Yoshimoto et al., *Science* 270: 1845-1847, 1995). These latter are a small granulocytic subset that triggers T and B cell responses by releasing IL-4 upon recognizing antigen via pre-bound IgE and IgG (Gauchat et al., *Nature* 365: 340-343, 1993).

SUMMARY OF THE INVENTION

In one aspect, the invention provides methods of attenuating an IgE-mediated response from basophils in a subject, such as histamine release, which are useful for treating an IgE-mediated disorder in the subject.

In one embodiment, the method involves administration of an agent that causes cross-linking of IgD pre-bound to the surface of basophils. In certain embodiments, such agent contains an anti-IgD antibody or a functional derivative thereof. The antibody or functional derivative may be conjugated to an additional substance to achieve effective cross-linking. Both monoclonal and polyclonal antibodies are contemplated by the invention.

In another embodiment, the method involves administration of an agent that targets, e.g., binds, an IgD receptor in basophils. In some embodiments, the agent contains a peptide having a heparin-binding consensus sequence.

The methods of the invention are useful for treating IgE-mediated disorders, such as asthma, atopic dermatitis, allergic rhinitis, allergic conjunctivitis, eczema, urticaria, food allergy and seasonal allergy.

In a further aspect, the invention provides a method of generating antimicrobial agents from human basophils. This method involves exposing basophils with surface-bound IgD to an agent that causes cross-linking of surface-bound IgD, and obtaining an antimicrobial compound from the supernatant of the basophils. In some embodiments, the cross-linking agent contains an anti-IgD antibody or a functional derivative thereof. The antibody or functional derivative may be conjugated to an additional material (such as beads or particles) to achieve effective cross-linking.

In still a further aspect, the invention provides a method of producing secretory IgD molecules from IgM$^+$IgD$^+$ B cells. The method involves exposing IgM$^+$IgD$^+$ B cells in culture to a mixture of B cell-stimulating factors which induce the production of secretory IgD molecules from the B cells. IgM$^+$IgD$^+$ B cells can be obtained from peripheral blood of any individual, including individuals suffering of hyper-IgD syndrome (RIDS), TNF receptor-associated periodic fever syndrome (TRAPS), Muckle-Wells syndrome (MWS), or periodic fever-aphthous stomatitis-pharyngitis-cervical adenitis (PFAPA) syndrome. In certain embodiments, the mixture of B cell-stimulating factors includes at least one of CD40L, BAFF and APRIL. In other embodiments, the mixture of B cell-stimulating factors includes a combination of IL15 and IL-21, or a combination of IL-2 and IL-21, in addition to one of CD40L, BAFF and APRIL.

BRIEF DESCRIPTION OF THE DRAWINGS

FIG. 1. Upper respiratory mucosa B cells generate IgD$^+$IgM$^-$ plasmablasts by undergoing Cµ-to-Cδ CSR in situ. (a) Proportions of IgD$^+$IgM$^-$ plasmablasts in various tissues calculated by immunofluorescence. PLN, peripheral lymph nodes; BM, bone marrow. (b) Diagram of CSR from Sµ to 94 δ. Germline Iµ-Cµ and Iµ-Cδ transcripts, σδ-Sµ switch circles, and post-switched Iµ-Cδ transcripts are shown. Arrows indicate primers. (c) Southern blots of σδ-Sµ switch circles PCR-amplified from mononuclear cells of various tissues and hybridized with σδ or Sµ probes. "Kb" stands for kilobases. (d) Germline Iµ-Cµ transcripts and germline or post-switch Iµ-Cδ transcripts in Reh IgD$^-$IgM$^+$ pre-B-like cells, 2E2 pre-germinal center IgD$^+$IgM$^+$ B cells, Ramos germinal center-like IgD$^-$IgM$^+$ B cells, and MM-M1 IgD$^+$IgM$^-$ plasma cells. Genomic β-actin was a loading control. One (1) of 3 experiments (bars indicate s.e.m.) was summarized in (a), whereas one (1) of 5 experiments yielding similar results was shown in each of (c) and (d).

FIG. 2. Cµ-to-Cδ CSR occurs through both T cell-dependent and T cell-independent pathways, requires AID, and leads to the production of IgD antibodies that bind to respiratory bacteria. (a) σδ-Sµ switch circles from circulating IgD$^+$IgM$^+$ B cells stimulated with or without CD40L, BAFF or APRIL plus IL-15 and IL-21 for 4 d. Genomic β-actin was a loading control. "Kb" stands for kilobases. (b, c) Flow cytometric analysis of surface IgD and IgM and ELISA of secreted IgD from circulating IgD$^+$IgM$^+$ B cells stimulated as in (a) for 7 d. Control indicates medium alone. (d) Flow cytometric analysis of CD19, IgM and IgD on peripheral blood IgD$^+$IgM$^+$ B cells used for class switch experiments. Gray histogram shows an isotype-matched control. (e) IgD and IgM expression on peripheral blood IgD$^+$IgM$^+$ B cells exposed to CD40L, BAFF or APRIL and a combination of IL-2 plus IL-21 for 7 days. (f) Results from ELISA assays of IgD secreted by peripheral blood IgD$^+$IgM$^+$ B cells stimulated as in (e). (g) Percentage of circulating IgD$^+$IgM$^-$ B cells in a healthy donor and patients with TNFSF5 (HIGM1), AICDA (HIGM2), TNFRSF5 (HIGM3), TNFRSF13b (CVID) or MVK (RIDS) gene defects. (b) Binding of secreted IgD to MID, CPS, LPS, *Moraxella catarrhalis*, and *Haemophilus influenzae* type a or type b as determined by ELISA. IgD secretion was obtained by incubating circulating IgD$^+$IgM$^+$ B cells with or without BAFF, IL-15 and IL-21 for 7 d. One of 5 experiments yielding similar results was shown in each of (a), (b), (d), (e) and (g), whereas 3 experiments were summarized in each of (c) and (0 (bars indicate s.e.m., *, p<0.05).

FIG. 4. IgD binds to basophilic and mast cell lines in vitro. (a) Binding of monoclonal IgD (50 µg/ml) to various lymphoid and myeloid cell lines. A F(ab')$_2$ pAb was used to detect IgD. Mo, MC and Basø indicate monocytic, mast cell and basophilic cell lines, respectively. (b) Binding of increasing amounts (0.5, 5 and 50 µg/ml) of monoclonal IgD to the mast cell line HMC-1 and binding of monoclonal IgD (50 µg/ml) to the basophilic cell line KU812 before and after treatment with IL-4 for 1 d and with IL-3 for 4 d. Control indicates medium alone. A F(ab')$_2$ pAb was used to detect IgD. Gray histogram depicts background fluorescence of cells that were not incubated with monoclonal IgD. (c) Binding of fluorochrome-conjugated monoclonal IgD to HMC-1 or KU812 cells in the presence of increasing amounts (0, 5, 50, 250 or 1000 µg/ml) of unlabeled monoclonal IgD. (d) Binding of untreated or denatured monoclonal IgD (50 µg/ml) to HMC-1 cells pre-incubated or not with IgG, IgA, IgE, mannose, mannan, trypsin, pepsin, papain, or papain plus leupeptin. A F(ab')$_2$ pAb was used to detect IgD. In all the experiments dead cells were excluded using 7-AAD staining. Three experiments were summarized in (a) (bars indicate s.e.m.), whereas one of 3 experiments yielding similar results was shown in each of (b)-(d).

FIG. 5. Basophils release immunostimulating and pro-inflammatory factors upon IgD cross-linking. (a) Flow cytometry analysis of CD63 on basophils exposed to microbeads alone (control), microbead-bound monoclonal anti-IgD, or microbead-bound monoclonal anti-IgE for 30 min or 5 h in the presence or absence of IL-3. (b) Results from ELISA assays of histamine from basophils exposed to microbeads alone (open bar), microbead-bound monoclonal anti-IgD (gray bar), microbead-bound monoclonal anti-IgE (black bar), or microbead-bound isotype-matched control monoclonal antibody (striped bar) for 30 min in the presence or absence of IL-3. (c) Results from ELISA assays of IL-4, IL-13 or BAFF from basophils exposed to microbeads alone (open bar), microbead-bound monoclonal anti-IgD (gray bar), or microbead-bound monoclonal anti-IgE (black bar) for 16 h in the presence or absence of IL-3. IL-8 and CXCL10 were measured after 48 h. (d) Intracellular $Ca^{2+}$ levels of basophils treated as in (c). The arrow indicates addition of the cross-linking reagent and 0 sec indicates the start of the kinetic measurement. (e) IgM, IgA and IgG production by peripheral blood $IgD^+IgM^+$ B cells exposed for 7 d to basophils treated as in (c). One of 3 experiments yielding similar results was shown in each of (a) and (d), and three experiments were summarized in each of (b), (c) and (e) (bars indicate s.e.m.; *, $p<0.01$; **, $p<0.001$).

FIG. 6. Basophils release antimicrobial factors upon IgD cross-linking. (a) QRT-PCR of DEFB103A, CAMP, SPAG11A/F, and SPAG11D/G transcripts from basophils exposed to microbeads alone (control, open bar), microbead-bound monoclonal anti-IgD (gray bar), or microbead-bound monoclonal anti-IgE (black bar) for 6 h. PTX3 and CRP transcripts were measured after 16 h. mRNAs were normalized to ACTB mRNA. (b) Results from ELISA assays of LL-37 from basophils stimulated as in a in the presence or absence of IL-3 for 8 h. (c) Growth of *Moraxella catarrhalis* and *Haemophilus influenzae* type-a and type-b upon 2-h exposure to culture supernatants from basophils stimulated as in a for 8 h or 16 h. CFU, colony forming unit. Three experiments were summarized in each of (a)-(c) (bars indicate s.e.m.; *, $p<0.03$; , $p<0.02$; *, $p<0.01$).

FIG. 7. Increased IgD class-switched plasmablasts and IgD-armed basophils in inflamed tissues from patients with periodic fever syndromes. (a, b) Flow cytometric analysis of circulating B cells and $CD123^+FILA-DR^-$ basophils in a healthy subject and hyper-IgD patients with MVK (RIDS), unknown (PFAPA), NALP3/CIAS1/PYPAF1 (MWS) and TNFRSF1A (TRAPS) gene defects. Numbers indicate percentage of $IgD^+IgM^-$ B cells in $CD19^+$ B cells and of $CD123^+$ $HLA-DR^-$ basophils in mononuclear cells. (c) ELISA of TNF-α, and IL-1β from basophils cultured with IL-3 and microbeads alone (control, open bar), microbead-bound monoclonal anti-IgD (gray bar) or microbead-bound monoclonal anti-IgE (black bar) for 48 h in the presence or absence of monocytes. One of 3 experiments yielding similar results was shown in each of (a)-(d), whereas 3 experiments were summarized in (e) (bars indicate s.e.m.).

DETAILED DESCRIPTION OF THE INVENTION

Figure 3:
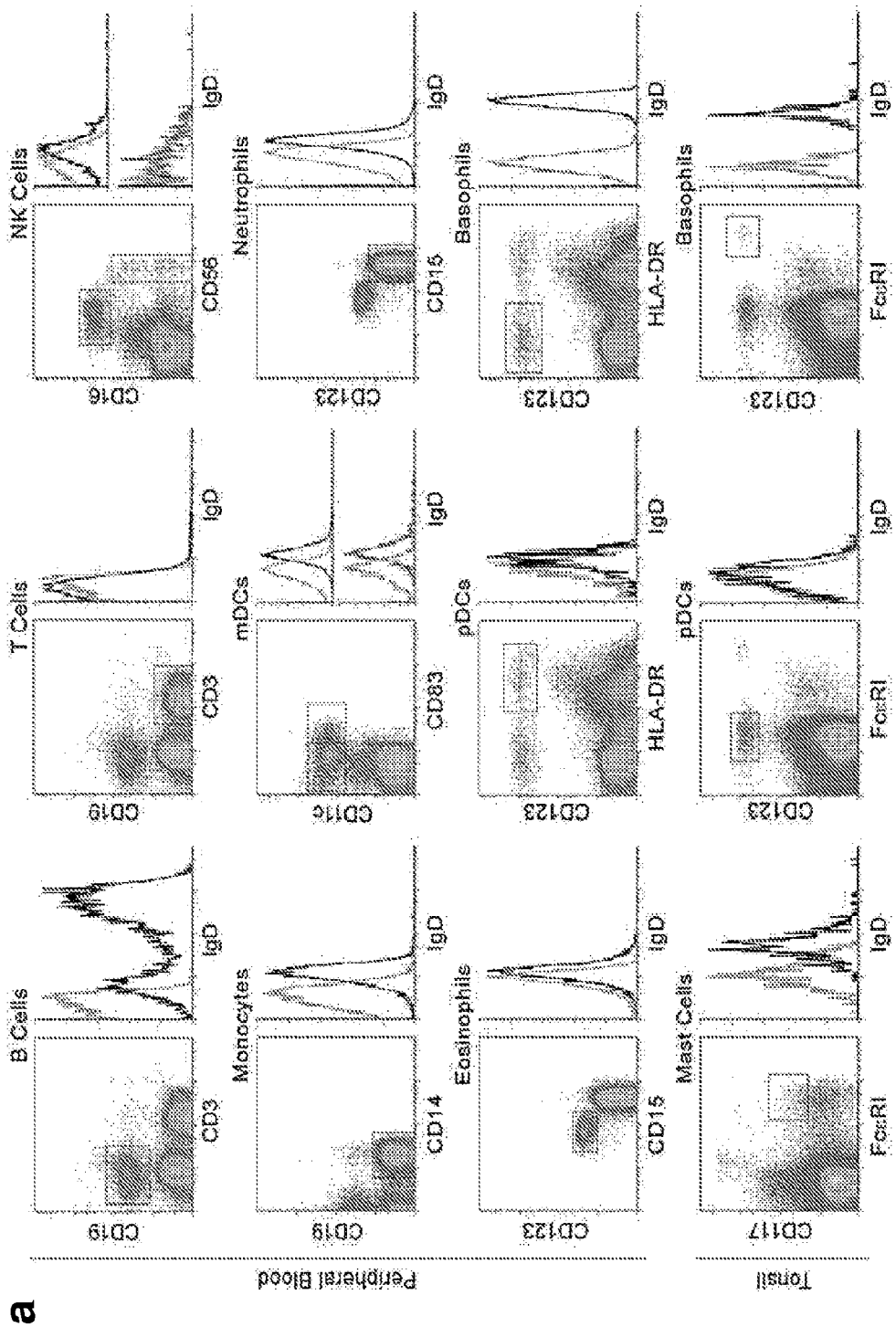
FIG. 3. IgD binds to basophils and mast cells in vivo. (a) Flow cytometric analysis of IgD on circulating or tonsillar CD19$^+$CD3$^-$ B cells, CD19$^-$CD3$^+$ T cells, CD16$^{high}$CD56$^{low}$ or CD16$^{low}$CD56$^{high}$ NK cells, CD19$^-$CD14$^+$ monocytes, CD11c$^+$CD83$^-$ or CD11c$^+$CD83$^+$ myeloid dendritic cells (mDCs), CD15$^+$CD123$^-$ neutrophils, CD15$^+$CD123$^{low}$ eosinophils, CD123$^+$HLA-DR$^+$ or CD123$^+$FcεR$^{low}$ plasmacytoid dendritic cells (pDCs), CD123$^+$HLA-DR$^-$ or CD123$^+$FcεRI$^+$ basophils, and CD117$^+$FcεRI$^+$ mast cells. Gray and black histograms depict control unstained cells and IgD, respectively. A F(ab')$_2$ pAb was used to detect IgD. Dead cells were excluded using 7-AAD staining. (b) Flow cytometry of IgD levels on circulating basophils before (black histogram) and after exposure to exogenous monoclonal IgD (10 µg/ml, brown histogram), treatment with acidic buffer (blue histogram), and treatment with acidic buffer followed by addition of exogenous IgD (red histogram). A F(ab')$_2$ pAb was used to detect IgD. Unstained basophils were used as control (gray histogram) and dead cells were excluded using 7-AAD staining. (e) Binding of labeled monoclonal IgD to circulating basophils stripped of endogenous IgD and incubated with 0 µg/ml (green histogram), 100 µg/ml (orange histogram) or 500 µg/ml (purple histogram) of unlabelled monoclonal IgD. A F(ab')$_2$ pAb was used to detect IgD. Unstained basophils were used as control (gray histogram) and dead cells were excluded using 7-AAD staining. (d) Flow cytometric analysis of IgD on viable (7-AAD$^-$) basophils, neutrophils, eosinophils, monocytes and myeloid dendritic cells (mDCs) from the peripheral blood of healthy individuals. A F(ab')$_2$ pAb was used to detect IgD. Mean fluorescence intensity (MFI) was the ratio between the fluorescence intensity of IgD-stained cells and the fluorescence intensity of unstained cells. The dashed line indicates average MFI for IgD on basophils. (e) Flow cytometric analysis of IgD, IgE, CD117 and FcεRI on viable (7-AAD$^-$) lung mast cells. A F(ab')$_2$ pAb was used to detect IgD. Controls (gray histograms) include cells stained with appropriate isotype-matched antibodies with irrelevant binding activity (CD117 and FcεRI) or unstained cells (IgE or IgD). (f) IgD, CD117 and FcεRI on viable circulating mast cells from two patients with mastocytoma. IgD was detected with a F(ab')$_2$ pAb and then analyzed on gated CD117$^+$FcεRF cells. FSC and SSC are forward and side scatters, respectively. One of 5 experiments yielding similar results was shown in each of (c) and (f).
Figure 3:
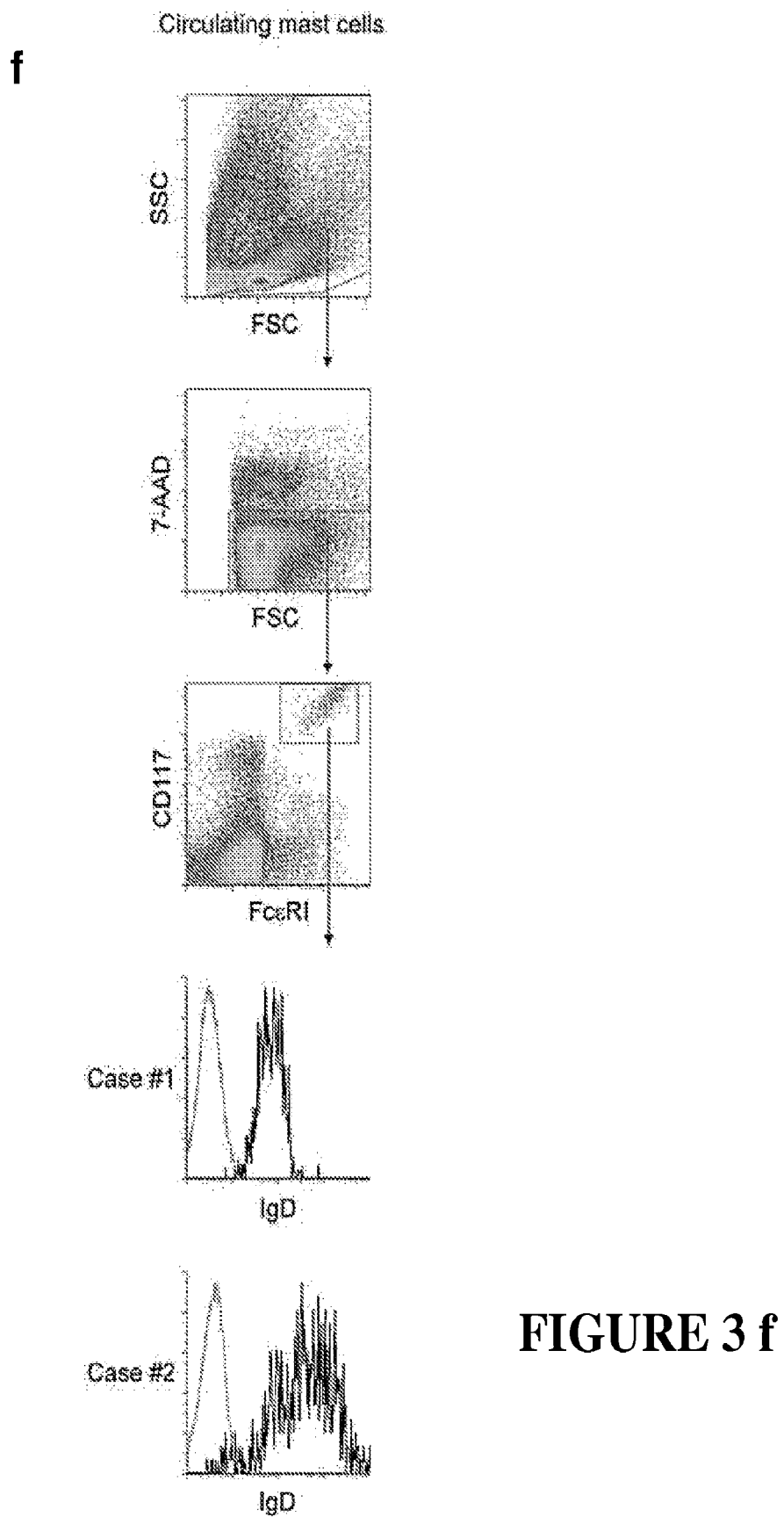

It has been identified in accordance with the present invention that human IgD molecules are generated from an IgM-to-IgD class switching process actively taking place in the upper respiratory tract mucosa B cells. It has been further identified that IgM-to-IgD class switching can be induced in vitro by exposing peripheral blood $IgM^+IgD^+$ B cells to a cocktail of B cell-stimulating factors. Additionally, IgD has been demonstrated herein to show strong reactivity for respiratory bacteria and to interact with circulating basophils through a calcium-fluxing receptor different from Fc receptors for IgG, IgA and IgE isotypes. Basophils, which are activated by cross-linking surface bound IgD, are shown herein to up-regulate the production and release of antimicrobial, opsonizing, inflammatory and antibody-inducing factors. On the other hand, basophil responses induced by IgE, such as release of histamine, have been found to be profoundly attenuated by cross-linking surface bound IgD. Various methods are provided by the invention and are described in more details below.

Methods of Attenuating IgE-Mediated Responses

In one embodiment, the invention provides a method of attenuating an IgE-mediated response from basophils.

Without being bound to any particular theory, it is believed that a basophil receptor with IgE-inhibitory properties is activated upon cross-linking of surface bound IgD. As a result, IgE-mediated basophil responses, such as histamine release, are dampened. Accordingly, IgE-mediated responses from basophils can be attenuated by employing an agent that causes cross-linking of surface bound IgD or an agent that targets the basophil receptor for IgD.

IgE is known to mediate allergic responses and is produced by B cells in both membrane-bound and secretory form. IgE binds to B-cells through its Fc region to a low affinity IgE receptor, known as FcεRII. Upon exposure to an allergen, B-cells bearing a surface-bound IgE molecule specific for the allergen are activated and further develop into IgE-secreting plasma cells. The secreted IgE molecules, which are specific for the allergen, circulate through the bloodstream and become bound to the surface of mast cells in tissue and basophils in bloodstream through the high affinity receptor, known as FcεRI. This binding by allergen-specific IgE, sensitizes the mast cells and basophils for the allergen. Subsequent exposure to the allergen causes cross-linking of FcεRI on basophils and mast cells, leading to up-regulation of the granular molecule CD63 and the release of a number of factors, such as histamine, platelet activating factors, eosinophil and neutrophil chemotactic factors, and cytokines such as IL-3, IL-4, IL-5 and GM-CSF.

The term "IgE-mediated response" from basophils, as used herein, refers to responses from basophils induced directly or indirectly by IgE, which can be observed (e.g., degranulation) and/or measured by up-regulation of the granular molecule CD63, or the release of one or more of histamine, platelet activating factors, eosinophil and neutrophil chemotactic factors, and cytokines such as IL-3, IL-4, IL-5 and GM-CSF.

In some embodiments, IgE-mediated responses underlying allergic reactions, such as degranulation, up-regulation of the granular molecule CD63, and/or the release of histamine from basophils, are attenuated as a result of administration of an appropriate agent.

The term "attenuating an IgE-mediated response", as used herein, is meant that the extent, occurrence and/or frequency of an IgE-mediated response is reduced by practicing the present method, e.g., by administering an agent which causes cross-linking of surface bound IgD on basophils), as compared to without administering the agent. The extent of reduction should be statistically significant and in certain embodiments, by at least 15%, 20%, 25%, 30%, 35%, 40%, 50%, 60%, 70%, 80%, 90% or greater.

Histamine is central to the pathogenesis of allergic disorders such as asthma and atopic dermatitis. Thus, by attenuating IgE-mediated responses such as histamine release, the present method is also effective in treating IgE-mediated disorders.

The term "IgE-mediated disorder", as used herein, means a condition or disease characterized by abnormal responses mediated by IgE, possibly due to overproduction of IgE and/or hypersensitivity of basophils or mast cells to IgE. Thus, as used herein, "IgE-mediated disorders" include allergic disorders, for example, asthma, atopic dermatitis, allergic rhinitis, allergic conjunctivitis, eczema, urticaria, food allergy and seasonal allergy, as well as anaphylactic shock, which can be caused by parental medication or bug bite.

The term "treating an IgE-mediated disorder", as used herein, is meant one or more of the clinical symptoms of a relevant disorder being ameliorated or reduced, the duration being shortened, the frequency of the occurrence of the symptoms being reduced, or the clinical symptoms being prevented from manifesting.

In accordance with the present invention, IgE-mediated responses are attenuated by administering to a subject an agent that causes cross-linking of IgD bound to the surface of basophils, or an agent that targets the IgD receptor on or in basophils.

By "subject" it is meant any mammalian subject in need of the treatment, including human subjects in particular, and cattle, sheep, goat, pigs, as well as companion animals such as dogs and cats. The subject may be someone who have had incidents of an IgE-mediated disorder, have repeated or periodic incidents of an IgE-mediated disorder, is suffering an incident of an IgE-mediated disorder, or is pre-disposed to suffer an IgE-mediated disorder.

In one embodiment, the present method involves administration of an agent that causes cross-linking of IgD bound to the surface of basophils. Abundant IgD has been demonstrated herein on the surface of both basophils and mast cells, but not any other leukocytes. Without limiting to any particular mechanism, it is believed that cross-linking surface-bound IgD simulates the activation of IgD-armed basophils under appropriate physiological conditions (e.g., upon an initial or subsequent exposure to an allergen in vivo).

In some embodiments, the agent that causes cross-linking of IgD is an anti-IgD antibody composition.

In certain embodiments, the anti-IgD antibody composition used in cross-linking contains a single anti-IgD antibody. In other embodiments, the anti-IgD antibody composition includes a mixture of two or more anti-IgD antibodies.

In one embodiment, the anti-IgD antibody composition contains an anti-IgD antibody specific for the Fab or Fab' fragment of IgD. In other embodiments, the anti-IgD antibody composition contains an anti-IgD antibody specific for the Fc region of IgD.

The anti-IgD antibody can be of an IgA, IgD, IgG, or IgM class immunoglobulins. In one embodiment, the anti-IgD antibody is IgG. In another embodiment, the anti-IgD antibody is IgM.

Anti-IgD antibodies are available through various commercial sources. Alternatively, anti-IgD antibodies can be generated by well-known methods. For example, the antibodies of the present invention can be generated using a protein preparation containing purified or partially purified IgD molecules, a recombinantly produced IgD molecule, fragments or portions thereof, as immunogen to immunize a host animal. Suitable host animals can include rabbit, chicken, rat, mouse, goat, sheep, cow, horse and the like.

Both polyclonal antibodies and monoclonal antibodies can be prepared using an immunized animal. The procedures for making polyclonal and monoclonal antibodies are well known in the art and can be found in, e.g., Harlow, E. and Lane, D., *Antibodies: A Laboratory Manual*, Cold Spring Harbor Press, 1988. Polyclonal antibodies can be readily purified from the serum of the immunized animal using a number of well known protein purification procedures such as affinity chromatography. Monoclonal antibodies can be prepared by following the standard hybridoma techniques (see e.g. Kohler et al., *Nature* 256:495, 1975). Briefly, the spleens of the immunized animal can be removed, and their lymphocytes are fused to an immortal cell line. The resulting hybridomas can be screened initially by binding affinity to IgD, which can be determined by various immuno assays such as ELISA. Antibodies that are found to bind IgD can be further tested for its ability to crosslink IgD bound to the surface of basophils. To screen for effective cross-linking ability, isolated basophils can be incubated with an anti-IgD antibody of interest, as well as an isotype-matched control antibody. The inhibition of histamine release and CD63 upregulation in the presence of the anti-IgD antibody of interest, as compared to the isotype control antibody, is indicative of the cross-linking ability of the antibody of interest.

Functional derivatives of the identified antibodies are also contemplated. "Functional derivatives" refer to antibody molecules or fragments that are derived from an originally identified anti-IgD antibody and that have retained the antigen specificity of the original antibody. Examples of functional derivatives include Fab, Fab', F(ab')$_2$ of an original antibody, single chain antibodies, deimmunized antibodies, and the like.

Deimmunized antibodies refer to antibodies derived from an original antibody, where the original antibody has been modified to reduce immunogenicity to an intended recipient. For example, for use in humans, anti-IgD antibodies raised in a non-human animal can be "humanized" to reduce the immunogenicity of the antibodies to human recipients. To illustrate, a monoclonal antibody raised in mice can be "humanized" by making a mouse-human chimeric antibody having the original variable region of the murine mAb, joined to the constant region of a human immunoglobulin. Chimeric antibodies and methods for their production have been well documented in the art. See, e.g., Cabilly et al., European Patent Application 125023 (published Nov. 14, 1984); Neuberger et al., PCT Application WO 86/01533, among others. Alternatively, humanization of a non-human antibody molecule can be achieved by transferring the six CDRs from the antibody molecule (donor framework region) to an acceptor framework region of a human antibody molecule, while retaining the specificity of antigen binding of the original non-human antibody molecule. See, for example, Queen et al., *PNAS* 86:10029-10033 (1988); Riechmann et al., *Nature* 332:323-327 (1988). Additional options for deimmunizing an antibody include generating fully human antibodies by immunizing an animal reconstituted with a human immune system. For example, mice reconstituted with a human immune system, or "humanized mice", have been described in the art, e.g., Pearson et al., *Current Protocols Immunolgoy*, Supplement 81, 15.21.1-15.21.21 (2008); Giassi et al., *Exp. Biol. Med.* 233: 997-1012 (2008); Shultz et al., *Nat Rev Immunol* 7:118-30 (2007); and Melkus et al., *Nature Medicine* 12, 1316-1322 (2006). Non-human animals genetically engineered to contain one or more human or humanized immunoglobulin loci to produce human or humanized immunoglobulins have also been described by, e.g., by Bruggemann et al., *Curr Opin Biotechnol* 8(4): 455-8 (1997); Lonberg et al., *Int Rev Immunol* 13(1):65-93 (1995); Neuberger et al., *Nature* 338: 350-2 (1989), and U.S. Publication 20030017534A1.

In some embodiments, the anti-IgD antibody or a functional derivative thereof used in the administration is a multivalent molecule, i.e., a molecule that binds two or more antigen (IgD in this case) which permits efficient cross-linking. For example, an anti-IgD antibody of the IgM class, may be developed and used. Methods of engineering multivalent antibodies have been documented in the art; e.g., U.S. Pat. No. 7,129,330; Wu, "Engineering Multivalent Antibody Fragments for In Vivo Targeting", in a book titled "Antibody Engineering: Methods and Protocols", pages 209-225, Volume 248 of Methods in Molecular Biology Series (2003), Print ISBN: 978-1-58829-092-2.

In other embodiments, an anti-IgD antibody or a functional derivative thereof can be further modified to enhance its ability to cross-link surface bound IgD, e.g., by conjugating to a material wherein multiple anti-IgD antibody molecules are attached to one unit of the material to permit efficient cross-linking. Suitable materials include, e.g., microbeads and nanoparticles, among others.

In addition to an anti-ND antibody, agents that bind and cross-link surface bound IgD also include, for example, the IgD-binding domain (peptide 962-1200) of *Moraxella catarrhalis* or *Haemophilus influenzae* immunoglobulin D binding protein, conjugated to a carrier. These IgD-binding proteins have been described in the art; see, e.g., "Isolation and characterization of a novel IgD-binding protein from *Moraxella catarrhalis*," *J. Immunol,* 2001 Aug. 15; 167(4): 2112-2120; "Structure and immunological action of the human pathogen *Moraxella catarrhalis* IgD-binding protein," *Crit. Rev Immunol.* 2006; 26(4):353-76; U.S. Pat. No. 7,115,271 (disclosing isolation and cloning of the IgD-binding protein from *Haemophilus influenza*); and U.S. Pat. No. 7,470,432 (disclosing isolation and cloning of the IgD-binding protein from *Moraxella catarrhalis*). By "IgD-binding domain" it is meant a fragment (e.g., an extracellular soluble portion) of these IgD-binding proteins that is responsible for binding to IgD. The conjugation of the IgD binding domain of these IgD-binding proteins to a carrier molecule (such as protein or lipid) can be achieved using standard methods; see, e.g., Carter J M, *Methods Mol. Biol.* 1994; 36:155-91.

In another embodiment, the present method involves administration of an agent that targets the IgD receptor on or in basophils. IgD has been demonstrated herein to interact with circulating basophils through a calcium-fluxing receptor different from Fc receptors for IgG, IgA and IgE isotypes. Based on hydrophobicity analysis provided herein, it is believed that heparin is a basophil receptor for IgD. The expression of heparin is mostly restricted to basophils and mast cells, and similar to histamine, heparin is stored in the basophils' granules.

By "targeting" the IgD receptor, it is meant that the agent either binds the IgD receptor directly and optionally also cross-links the IgD receptor, or activates the IgD receptor indirectly by binding and aggregating the ligand (i.e., IgD) bound to this receptor. In some embodiments, for example, an antibody specific for the IgD receptor or a functional derivative thereof, which binds and causes cross-linking of the IgD receptor, can be used. Antibodies specific for heparin can be generated using well known methods such as those described above.

In other embodiments, peptides that contain a heparin-binding consensus sequence are candidate agents for "targeting" the IgD receptor. As used herein, a "heparin-binding consensus sequence" is defined by the 8-mer amino acid sequence as set forth in SEQ ID NO: 4. Sequences that differ from SEQ ID NO: 4 by substitution, addition or deletion of one or two amino acids are also considered as a heparin-binding consensus sequence. For example, the 7-mer amino acid sequence as set forth in SEQ ID NO: 4 is also considered herein as a heparin-binding consensus sequence.

Peptides which contain a heparin-binding consensus sequence suitable for use in the present invention are at least 8 or 9 amino acids in length. In some embodiments, the peptide contains at least 15 amino acids. In other embodiments, the peptide contains at least 20 amino acids. In certain embodiments, the peptide contains no more than 200 amino acids. In other embodiments, the peptide contains no more than 100 amino acids. In still other embodiments, the peptide contains no more than 50 amino acids.

The peptides which bind to heparin can be additionally modified to provide for or enhance the ability to crosslink heparin, e.g., by conjugating a peptide to a carrier molecule (e.g., protein or lipid). Candidate peptides can be tested in an in vitro assay, such as those described herein, to confirm its efficacy in attenuating the IgE-mediated histamine release from basophils, for example, before a therapeutic use in a human subject.

Agents that cause cross-linking of pre-bound IgD or that target the IgD receptor, as described above, can be used in conjunction with one or more additional suitable agents, such as any suitable anti-allergic agents.

According to the present invention, an agent that causes cross-linking of pre-bound IgD or that targets the IgD receptor can be combined with a pharmaceutically acceptable carrier prior to administration to a subject. As used herein, a pharmaceutically acceptable carrier includes any and all solvents, dispersion media, isotonic agents and the like. Except insofar as any conventional media, agent, diluent or carrier is detrimental to the recipient or to the therapeutic effectiveness of the active ingredients contained therein, its use in practicing the methods of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

An active ingredient, i.e., an agent that causes cross-linking of pre-bound IgD or that targets the IgD receptor, can be combined with the carrier in any convenient and practical manner, e.g., by admixture, solution, suspension, emulsification, encapsulation, absorption and the like, and can be made in formulations such as tablets, capsules, powder, syrup, suspensions, liquid drops, that are suitable for injections, implantations, inhalations, ingestions or any other appropriate application.

The active agents of the present invention can be administered to the subject by standard routes, including the oral, ophthalmic, nasal, topical, transdermal, parenteral (e.g., intravenous, intraperitoneal, intradermal, subcutaneous or intramuscular) route.

An active agent is administered to a subject at a "therapeutically effective amount", which means the amount required to effect a significant attenuation of IgE-mediated responses such as release of histamine or u-regulation of CD63. Precise dosages depend on the type of formulations, the route of administration, the timing and frequency of the administration, and the condition of the recipient, for example. The precise dosage to be therapeutically effective can be determined by those skilled in the art including a physician.

Method of Obtaining Antimicrobial Agents by Activating Basophils

In a further aspect, the invention provides a method of generating antimicrobial agents by activating human basophils with an agent that causes cross-linking of surface-bound IgD, and identifying an antimicrobial compound from the supernatant of activated basophils.

As demonstrated hereinbelow, IgD cross-linking by a bead-conjugated anti-IgD antibody quickly up-regulates the production and release of antimicrobial agents from human basophils. This up-regulation is highly specific to IgD, because IgE cross-linking through a bead-conjugated anti-IgE antibody is not nearly as efficient. Cathelicidin, β-defensin 3, sperm-associated antigen-11, pentraxin-3 and C-reactive transcripts and proteins are among the antimicrobial agents that have been detected in the total RNA and supernatants from IgD-stimulated basophils. Thus, IgD cross-linking permits identification of new antimicrobial compounds or peptides from activated basophils.

To practice this aspect of the invention, human basophils can be purified from human peripheral blood using known methods. See, e.g., MacGlashan and Lichtenstein, *J Immunol.* 1980; 124: 2519-2521; Gibbs et al., *Inflamm. Res.* (1997) 46: 137-142 (describing a three-step process for purification of human basophils from buffy coats without the need for positive selection based on $Fc_\epsilon RI$); and Mita et al., *Prostaglandins Leukot Essent Fatty Acids* (1993) 49(4):783-8 (describing a procedure based on ficoll gradient purification in combination with negative selection), among others. In addition, commercial kits for purification of basophils are also available. For example, two negative selection kits for purification of human basophils are available from Miltenyi Biotech, Friedrich-Ebert-Straße 68, 51429 Bergisch Gladbach, Germany.

By "purified" basophils, it is meant that basophils account for at least 70%, 75%, 80%, 85%, 90% or more of the cell population. Morphological and functional criteria, as well as cell surface markers, for identifying basophils are well known in the art.

In addition to basophils purified from human peripheral blood, basophilic cell lines can be employed as well. Various basophilic or pre-basophilic cell lines are available to those skilled in the art and can be used in the present invention. Examples of suitable cell lines include human basophilic cell lines KU812, basophil-like cell line LAMA-84, in vitro differentiated human basophils from bone marrow progenitors (*Leukemia Research* 10(10), 1241-1248, 1986), and human mast cell lines HMC-1, LAD-2.

To produce antimicrobial agents in accordance with the present invention, basophils are exposed to a composition containing an anti-IgD antibody or a functional derivative thereof, wherein the composition causes cross-linking of IgD surface bound to basophils. In some embodiments, the anti-IgD antibody or derivative thereof is conjugated to a solid material to enable the anti-IgD antibody to cross-link surface bound IgD. In other embodiments, the anti-IgD antibody is not directly conjugated to a solid material, but is used in conjunction with a second antibody which is specific for the anti-IgD antibody and is conjugated to a solid material. Suitable solid materials for use in conjugation include beads (such as microbeads or magnetic beads both of which are commercially available), particles including nanoparticles, agarose, among others. The procedures for conjugating an antibody to a solid material are also known in the art.

The amount of an anti-IgD antibody to use to cross-link surface bound IgD generally is at least 5, 10, 15, 20, 25, 30, 35, 40, 45, 50, or 100 µg/ml, or any value falling between the any of the two values listed. In some embodiments, the amount of an anti-IgD antibody used is about 25 µg/ml.

A cross-linking antibody composition can be used alone or in combination with additional agent(s) suitable for activating basophils, including for example, IL-3.

Crude supernatant of anti-IgD-activated basophils can be clarified by filtration or centrifugation to remove particulates and made compatible with chromatography analysis. To avoid precipitation of samples on chromatography columns, the solubility of supernatant samples can be tested over a range of elution solvent compositions based on the method of chromatography to be chosen.

Clarified samples can be separated by preparative liquid chromatography methods to identify fractions with antimicrobial activity using standard antimicrobial assays. Typically, chromatography methods that are compatible with one another and with the downstream antimicrobial assay are chosen. Several different chromatography methods can be combined if necessary to improve resolution and yield. In some embodiments, purification is achieved using one or more or all three of the following chromatography methods: gel-filtration chromatography, ion-exchange chromatography, and reverse-phase HPLC.

After chromatography, a suitable antimicrobial assay, such as a broth microdilution assay described in the examples hereinbelow or a semi-solid agar-based method (Xu et al., *Toxicon* 47:249-253, 2006), can be used to test the antimicrobial activities of the fractions derived from basophil supernatants. The fraction or fractions containing reproducible antimicrobial activities are then subjected to liquid chromatography-mass spectrometry (or "LC-MS") to identify antimicrobial peptide sequence and compare with known antimicrobial peptides.

Method of Making IgD

In still a further aspect, the invention provides a method of producing secretory IgD molecules from IgM$^+$IgD$^+$ B cells by exposing such B cells to a mixture of B cell-stimulating factors.

IgD produced in a recombinant expression system may not carry proper post-translational modifications (such as glycosylation) which may be important for its function. For example, specific glycosylation structures may be required for IgD to interact with its receptor(s). In addition, it is advantageous to induce, express and clone IgD antibodies from primary B cells of patients with low IgE responses to allergens or any other patients characterized by an abnormal IgD or IgE response, such as patients suffering hyper-IgD syndrome (BIDS), TNF receptor-associated periodic fever syndrome (TRAPS), Muckle-Wells syndrome (MWS), and periodic fever-aphthous stomatitis-pharyngitis-cervical adenitis (PFAPA) syndrome. IgD antibodies from these patients may have F(ab)-dependent allergen-blocking features in addition to Fc-dependent IgE-inhibiting features.

IgM$^+$IgD$^+$ B cells can be obtained from human peripheral blood using known methods. For examples, B cells can be obtained from peripheral blood, then depleted of antigen-experienced plasmablasts using CD27-targeting microbeads (i.e., microbeads conjugated with an anti-CD27 antibody), as described hereinbelow to obtain IgM$^+$IgD$^+$ B cells. Alternatively, IgM$^+$IgD$^+$ B cells can be sorted by flowcytometry from B cells obtained from peripheral blood. IgM$^+$IgD$^+$ B cell lines can also be used, including e.g., pre-germinal center 2E2 cell line. 2E2 cell line is an subclone of the CL-01 IgM$^+$IgD$^+$ B-cell line. The 2E2 cell line is typically cultured in RPMI-1640 medium, and can be induced to undergo class switching, somatic hypermutation and complete differentiation in vitro. Information regarding the CL-01 cell line is available via the web site of Cornell Center for Technology Enterprise and Commercialization.

Purified IgM$^+$IgD$^+$ B cells are then exposed to a mixture of B cell-stimulating factors to induce production of secretory IgD. B-cell stimulator factors include, but not limited to, CD40 ligand (CD40L), B cell-activating factor of the TNF family (BAFF), the proliferation-inducing ligand and cytokine APRIL, IL-15, IL-2 and IL-21. Each of these factors has been well documented in the art and is available through commercial sources or recombinant production.

In accordance with the invention, the mixture of B cell-stimulating factors used to induce the production of secretory IgD includes at least one of CD40L, BAFF and APRIL. Additionally, the mixture contains a combination of IL15 and IL-21, or a combination of IL-2 and IL-21. Generally speaking, for each of CD40L, BAFF and APRIL, the amount used in the mixture can fall in the range of 50-2000 ng/ml, or 100-1000 ng/ml, or about 500 ng/ml. For each of IL2, IL-15 and IL-21, the amount used in the mixture can fall in the range of 10-500 ng/ml, or 20-200 ng/ml, or about 50-100 ng/ml.

IgM$^+$IgD$^+$ B cells can be cultured in the presence of a desirable mixture of B cell-stimulating factors using any appropriate media for culturing and maintaining B cells, and for a period time sufficient to induce adequate IgM secretion. A culture period of at least one or two days is appropriate, and can be as long as 4-8 days or longer.

IgD molecules secreted from the activated cells can be purified from the supernatant using any of the known protein purification techniques applicable for IgD.

In the following examples, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that changes may be made without departing from the scope of the present invention. The following description of exemplified embodiments is, therefore, not to be taken in a limited sense.

Example 1

IgD Class-Switched Plasmablasts Originate in the Upper Respiratory Mucosa

Human B cells have been reported to release IgD in the blood as well as respiratory, salivary, lacrimal and mammary secretions. Immunohistochemistry, light microscopy and flow cytometry techniques were used to elucidate the geography and phenotype of IgD$^+$IgM$^-$ B cells producing IgD. Unlike intestinal, hepatic, lymph nodal, splenic and hematopoietic tissues, tonsillar and nasal tissues were seen to harbor abundant IgD$^+$IgM$^-$ B cells that had topographic and morphologic features distinct from those of conventional IgD$^+$IgM$^+$ B cells (FIG. 1a). These latter cells occupied the follicular mantle but not the germinal center of secondary lymphoid follicles, had a small size, round shape, scant cytoplasm and large nuclei, and expressed both κ and λ IgL chains on their surface in addition to the pan-B cell molecules CD19, CD20, CD21, CD22, CD24, CD39, CD40, major histocompatibility complex (MHC) class I and class II molecules, BAFF-receptor (BAFF-R), transmembrane activator and CAML interactor (TACI), and the transcription factor Pax-5.

In contrast, IgD$^+$IgM$^-$ B cells were seen to populate both germinal center and extrafollicular areas, had an ovaloid-elongated shape, medium-large size, abundant cytoplasm containing $C_\delta$ IgH chains preferentially coupled with λ IgL chains, and small and often picnotic eccentric nuclei. These IgD$^+$IgM$^-$ plasmablasts accounted for up to 20-25% of antibody-forming plasma cells and for about 1.5-5% of total CD19$^+$ B cells in tonsils. In spite of their plasmacellular morphology, only a subset of IgD$^+$IgM$^-$ B cells expressed B lymphocyte-induced maturation protein-1 (Blimp-1) and B cell maturation antigen (BCMA), and virtually none of them expressed CD138 (or syndecan-1), three hallmarks of mature plasma cells. Furthermore, IgD$^+$IgM$^-$ plasmablasts retained surface Igs as well as CD19, CD20, CD21, CD22, CD24, CD39, CD40, MHC-I, MHC-II, BAFF-R, TACI and Pax-5, which are usually down-regulated by terminally differentiated plasma cells.

In addition to showing a bias for surface λ IgL chains, some or all IgD$^+$IgM$^-$ plasmablasts were observed to express the activation molecule CD5, the germinal center molecules CD10, CD38, CD77 and Ki-67, the effector-memory molecule CD27, as well as the DNA-editing enzyme AID, a hallmark of ongoing class switching. Similar IgD$^+$IgM$^-$ blasts were found in the peripheral blood, where they accounted for 0.5-1% of circulating CD19$^+$ B cells.

These data indicate that the upper respiratory mucosa generates local and circulating IgD$^+$IgM$^-$ plasmablasts specialized in IgD production. These cells express a complex phenotype that likely reflects a derivation from multiple follicular and extrafollicular precursors, including germinal center B cells.

Example 2

Upper Respiratory Mucosa B Cells Undergo CSR from $C_\mu$ to $C_\delta$ In Situ

B cells are known to express $C_H$ genes downstream of Cμ through a CSR reaction that relies on switch (S) regions (Chaudhuri et al., *Nat. Rev. Immunol.* 4: 541-552, 2004) Positioned upstream of each $C_H$ gene and an intronic (I) exon, S regions undergo germline transcription upon exposure of B cells to appropriate stimuli (Chaudhuri et al. (2004), supra). In addition to yielding $I_H$-$C_H$ transcripts, germline transcription renders S regions substrate for DNA modifications by the CSR machinery, including AID (Chaudhuri et al. (2004), supra). Processing of these modifications into double-stranded DNA breaks is followed by fusion of these breaks through the non-homologous end joining pathway and looping-out deletion of the intervening DNA (Chaudhuri et al. (2004), supra). Ultimately, CSR generates post-switch $I_\mu$-$C_H$ transcripts as well as an extrachromosomal S-S switch circle (FIG. 1b), which is a hallmark of ongoing CSR together with AID (see, e.g., Chaudhuri et al. (2004), supra).

Humans have a Cδ gene preceded by a S-like σδ region that mediates CSR from Cμ to Cδ. Using a nested polymerase chain reaction (PCR)-based strategy, extrachromosomal Sμ switch circles were identified herein in B cells from tonsils, but not from peripheral blood, spleen, bone marrow, lymph nodes or intestine (FIG. 1e). CSR from Cμ to Cδ was associated with active Cδ gene transcription, because both the pre-germinal center IgD$^+$IgM$^+$ B cell line 2E2 and tonsillar follicular mantle IgD$^+$IgM$^+$13 cells contained chimeric germline Iμ-Cδ transcripts in addition to conventional germline Iμ-Cμ transcripts (FIG. 1d).

Although expressing Iμ-Cμ transcripts, neither the pre-B IgD−IgM+ cell line Reh nor the germinal center IgD−IgM+ B cell line Ramos contained Iμ-Cδ transcripts. This observation indicates that germline Cδ gene transcription is a developmentally regulated process beginning at a pre-germinal center stage of mature B cell differentiation. Finally, post-germinal center IgD$^+$IgM$^-$ plasma cells lacked germline Iμ-Cμ transcripts, but contained post-switch Iμ-Cδ transcripts as a result of Sμ-to-σδ CSR-induced juxtaposition of the Iμ exon to Cδ exons. The identity of σδ-Sμ and Iμ-Cδ amplicons obtained from tonsillar IgD+ B cells was confirmed by DNA sequencing.

These findings support a conclusion that a subset of B cells actively undergoes CSR from $C_\mu$ to $C_\delta$ in the microenvironment of the upper respiratory mucosa.

Example 3

IgD CSR Requires AID and Occurs Via Multiple Pathways

It has been documented that CSR usually involves engagement of CD40 on follicular B cells by CD40 ligand on T cells or engagement of TACI on extrafollicular B cells by B cell-activating factor of the TNF family (BAFF) or a proliferation-inducing ligand (APRIL) from innate immune cells. Co-signals from cytokines are also required. IgD$^+$IgM$^+$ B cells were observed herein to induce σ$_\delta$-S$_\mu$ switch circles, lose surface IgM, and secrete IgD upon exposure to CD40L, BAFF or APRIL plus either IL-15 and IL-21 or IL-2 and IL-21 (FIGS. 2a-2c and 2d-2f), three cytokines produced by dendritic cells and T cells. These effects were not due to expansion of IgD$^+$IgM$^-$ plasmablasts present at the onset of the culture, because fresh IgD$^+$IgM$^+$ B cells lacked σ$_\delta$-S$_\mu$ switch circles. In addition, CD40L, BAFF or APRIL alone or combined with IL-2, IL-4, IL-10, IL-13, IL-15 and/or IL-21 elicited neither loss of surface IgM nor secretion of IgD in spite of being powerful inducers of B cell survival and proliferation (FIGS. 2d-2f). The specificity of in vitro induced σδ-Sμ switch circles was confirmed by sequencing.

The IgD-inducing function of CD40L, BAFF and APRIL was further studied in patients with primary immunodeficiencies. TNFSF5 and TNFRSF5 gene defects, which have been reported to impair CD40L and CD40 signaling in patients with hyper-IgM type-1 (HIGM1) and HIGM3 syndromes (Cunningham-Rundles et al., *Nat. Rev. Immunol.* 5: 880-892, 2005), were observed herein to lead to a reduction of both circulating and follicular IgD$^+$IgM$^-$ plasmablasts, but spared extrafollicular IgD$^+$IgM$^-$ plasmablasts (FIG. 2g). This result supports the conclusion that CD40L-CD40 interaction is indispensable for the generation of systemic but not mucosal IgD-producing effector-memory B cells.

TNFRSF13b gene defects, which have been reported to impair TACI signaling in a subset of patients with common variable immunodeficiency (CVID) (Garibyan et al., *J. Clin. Invest.* 117: 1550-1557, 2007; Zhang et al., *J. Allergy Clin. Immunol.* 120: 1178-1185, 2007), were also observed herein to associate with a reduction of circulating IgD$^+$IgM$^-$ plasmablasts. AICDA gene defects, which have been reported to impair AID function in patients with HIGM2 syndrome (Cunningham-Rundles et al., *Nat. Rev. Immunol.* 5: 880-892, 2005), caused a reduction of both circulating and follicular IgD$^+$IgM$^-$ plasmablasts. This reduction was linked to a lack of functional AID protein, because B cells from HIGM2 patients neither induced σδ-Sμ switch circles nor underwent loss of surface IgD upon exposure to appropriate stimuli. HIGM2 as well as HIGM3 syndromes were observed herein to associate with an increased generation of double-producing IgD$^+$IgM$^+$ plasmablasts at both follicular and extrafollicular mucosal sites, which is believed to reflect the activation of a CSR-independent pathway for compensatory IgD synthesis. Thus, these results support the conclusion that IgD CSR requires AID and occurs via both T cell-dependent (TD) and T cell-independent (TI) pathways in vivo.

Example 4

IgD Recognizes Respiratory Bacteria

Given their origin from the upper respiratory mucosa, the inventors believed that IgD$^+$IgM$^-$ plasmablasts may release IgD antibodies that recognize airborne bacteria. Consistent with this notion, IgD secreted by stimulated IgD$^+$IgM$^-$ plasmablasts bound to the Gram-negative bacteria *Moraxella catarrhalis* and *Haemophilus influenzae* type a and type b (FIG. 2h).

Example 5

IgD Binds to Circulating Basophils

Humans have 15-300 μg/ml of circulating IgD (Rowe et al., *J. Exp. Med.* 121: 171-199, 1965; Brandtzaeg et al., *Immunol. Rev.* 171: 45-87, 1999). To elucidate the function of circulating IgD, its in viva interaction with Fc receptor-blocked peripheral blood leukocytes was examined by flow cytometry. Using a highly specific polyclonal anti-IgD antibody fragment with no Fe receptor binding activity and no IgG cross-reactivity, it was found that basophils had abundant surface IgD, whereas T cells, NK cells, monocytes, myeloid dendritic cells, neutrophils, eosinophils and plasmacytoid dendritic cells exhibited no or little surface IgD (FIG. 3a). Basophils were consistently positive for surface IgD binding also when stained with a whole monoclonal anti-IgD antibody.

IgD was detected not only on the surface, but also in the cytoplasm of circulating basophils as well as mucosal basophils, indicating that basophils internalize IgD-bound immunocomplexes. Addition of exogenous monoclonal IgD did not increase the IgD binding level on basophils, indicating saturation of binding sites by endogenous IgD (FIG. 3b). However, monoclonal IgD could bind to basophils following stripping of endogenous IgD. Finally, addition of increasing amounts of unlabeled monoclonal IgD progressively diminished the binding of labeled monoclonal IgD to basophils stripped of endogenous IgD (FIG. 3c).

Mast cells, a mucosal immunocyte functionally related to basophils, also stained positive for IgD (FIGS. 3d-3f).

The specific tropism of IgD for basophils and mast cells was confirmed in vitro by showing binding of physiological concentrations (from 0.5 to 50 µg/ml) of polyclonal or monoclonal IgD molecules to the pre-basophilic cell line KU812 and to the mastocytoid cell lines HMC-1 and LAD-2 (see, e.g., FIG. 4a). This binding was highly specific, because it was detected with either polyclonal or monoclonal anti-IgD reagents with no cross-reactivity for IgG. Except for the monocytic cell line U937, none of the T, NK and myeloid cell lines tested showed significant binding of IgD. KU812 and LAD-2 cells up-regulated IgD binding upon exposure to IL-3 and/or IL-4 (see, e.g., FIG. 4b), two cytokines reportedly involved in basophil and mast cell differentiation (Dawicki et al., Curr. Opin. Immunol. 19: 31-38, 2007; Karasuyama et al., Nat. Rev. Immunol. 9: 9-13 (2009)). Indeed, in addition to augmenting their IgD-binding activity, IL-3-stimulated KU812 cells up-regulated surface CD124 (IL-4 receptor) and FcεRI (IgE receptor) and down-regulated surface CD117 (c-kit receptor), whereas IL-4-stimulated LAD-2 cells up-regulated surface CD123 (IL-3 receptor). Binding of labeled IgD to KU812 or HMC-1 cells was saturable and could be competed by unlabelled IgD, but not IgG or IgE, whereas IgA had a minimal inhibitory effect (FIGS. 4c-4d).

Both IgA and IgD are known to be highly mannosylated. Both mannose and mannan slightly inhibited IgD binding to target cells (FIG. 4d), indicating that IgD could possibly utilize mannose to enhance its binding to basophils and mast cells. Finally, IgD binding was abolished by denaturing IgD or by pre-treating target cells with trypsin and papain, but not pepsin (FIG. 4d). The results support the conclusion that IgD binds to basophils and mast cells through a protease-sensitive, IL-3/IL-4-inducible receptor distinct from IgG, IgA and IgE receptors.

Example 6

IgD Binding to Basophils is Evolutionarily Conserved

In flow cytometric studies conducted with specific monoclonal antibodies, it was found that catfish also exhibited circulating granular leukocytes armed with surface IgD but not IgM. These IgD$^+$IgM$^-$ granulocytes contained neither transcripts for the T cell antigen receptor nor transcripts for transmembrane and secreted $C_\delta$ and $C_\mu$ IgH chains and did not react with a specific monoclonal antibody to neutrophils, indicative of their affiliation to a distinct granulocytic subset. These data support the conclusion that binding of B cell-derived IgD to granulocytes is part of an evolutionarily conserved and potentially important immune pathway.

Example 7

Basophils Produce B Cell-Activating Factors Upon IgD Cross-Linking

IgD on basophils were crosslinked with a specific monoclonal anti-IgD antibody in the presence or absence of the basophil maturation factor IL-3. Controls were performed using an irrelevant antibody or an antibody to IgE. This antibody to IgE has been reported to bind basophils through a high-affinity FcεRI receptor that triggers degranulation and histamine release upon cross-linking (Dawicki et al., Curr. Opin. Immunol. 19: 31-38, 2007; Karasuyama et al., Nat. Rev. Immunol 9: 9-13 (2009)).

Unlike IgE cross-linking, IgD cross-linking elicited neither surface up-regulation of the granular molecule CD63 nor histamine release irrespective of the presence of IL-3 (FIG. 5a-5b). Although less efficient than IgE cross-linking in inducing membrane-bound CD40L and BAFF, IgD cross-linking was more efficient than or as efficient as IgE cross-linking in inducing soluble IL-4, IL-13 and BAFF, membrane-bound APRIL, and soluble IL-8 and CXCL10 (FIG. 5c), two chemokines active on monocytes, neutrophils and T cells. These effects were potentiated by IL-3.

Although unable to induce degranulation, IgD cross-linking triggered intracellular calcium fluxes more sustained than those induced by IgE (FIG. 5d). The basophil-stimulating activity of IgD was further confirmed by experiments showing that, in the presence of IgD cross-linking, basophils pretreated or not with IL-3 acquired the capability of inducing IgM secretion as well as IgG and IgA class switching in B cells (FIG. 5e). The B cell-licensing function of IgD-cross-linked basophils was largely dependent on BAFF and APRIL, because it was abolished by a soluble TACI-Ig decoy receptor.

These results indicate that IgD stimulates basophils through a calcium-fluxing receptor that induces multiple cytokines, including the B cell-activating factors IL-4, IL-13, BAFF and APRIL.

Example 8

Basophils Produce Antimicrobial Factors Upon IgD Cross-Linking

IgD-cross-linked basophils were also found to induce antimicrobial, opsonizing and alarm-signaling factors, including DEFB103A, CAMP, SPAG11A/F, SPAG11D/G, PTX3 and CRP transcripts for β-defensin 3, cathelicidin, sperm associated antigen 11 (SPAG11) A/F isoforms, SPAG11 DIG isoforms, PTX3, and C-reactive protein (CRP) (FIG. 6a). These factors have been described in the art (Yamaguchi et al., 169: 2516-2523, 2002; Oppenheim et al., Curr. Opin. Immunol. 17: 359-365, 2005; Garlanda et al., Annu. Rev. Immunol. 23: 337-366, 2005). In addition, IgD-stimulated basophils released the cathelicidin-derived peptide LL-37 (FIG. 6b). Consistent with these results, supernatants from IgD-cross-linked basophils inhibited the replication of Moraxella catarrhalis and Haemophilus influenzae (FIG. 6c). In contrast, IgE cross-linked basophils had little or no antimicrobial activity. It can be concluded that IgD cross-linking activates powerful antimicrobial, opsonizing and alarm-signaling programs in basophils.

Example 9

Basophils are Dysregulated in Hyper-IgD Patients with Periodic Fever

To elucidate the relationship between IgD and basophils in vivo, IgD class-switched B cells and IgD-armed basophils were analyzed in hyper-IgD syndrome (HIDS), TNF receptor-associated periodic fever syndrome (TRAPS), Muckle-Wells syndrome (MWS), and periodic fever-aphthous stomatitis-pharyngitis-cervical adenitis (PFAPA) syndrome.

Although characterized by diverse genetic defects, these autoinflammatory disorders are considered to share a perturbation of the mechanisms that initiate and control the inflammatory reaction. Such a perturbation causes periodic attacks of fever and tissue damage as well as abnormal IL-1 and TNF-α release and elevated IgD production (Preud'homme et al., *Mol. Immunol.* 37: 871-887, 2000; Ryan et al., *Curr. Top. Microbial. Immunol.* 321: 169-184, 2008).

It was observed herein that compared to healthy subjects, HIDS, TRAPS, MWS, and PFAPA syndrome patients had more circulating and mucosal IgD$^+$IgM$^-$ plasmablasts (FIGS. 7a-7b), indicating that switching from IgM to IgD is augmented in autoinflammatory syndromes. Additionally, fewer circulating but more mucosal IgD-armed basophils and possibly mast cells were observed in these disorders, supporting the notion that elevated IgD production enhances mucosal homing and proliferation of basophils and mast cells. Consistent with this notion, mucosal basophils were found to exhibit signs of hyperactivation, including strong BAFF, APRIL and LL-37 expression.

The inventors also tested whether IgD triggering would increase IL-1β and TNF-α production by basophils. IL-1β and TNF-α have been reported to be IgD-inducible pro-inflammatory cytokines involved in autoinflammatory syndromes (Ryan et al., *Curr. Top. Microbial. Immunol.* 321: 169-184, 2008; Drenth et al., *Immunology* 88: 355-363, 1996). It was found herein that in the presence of IgD cross-linking, IL-3-treated basophils from healthy subjects released both IL-1β and TNF-α and this release further increased in the presence of monocytes (FIG. 7c), a cell type heavily involved in inflammation. In contrast, IgE cross-linking had little or no IL-1β- or TNF-α-inducing activity.

Overall, the data indicate that IgD and basophils orchestrate an ancestral surveillance system at the interface between immunity and inflammation. A dysregulation of this system could contribute to the pathogenesis of autoinflammatory syndromes with periodic fever.

Example 10

IgD Regulates IgE-Induced Basophil Functions

This example describes experiments conducted to investigate whether IgD could regulate the responses of basophils to IgE by comparing the responses of basophils stimulated by IgD and IgE crosslinking simultaneously with those stimulated by IgE crosslinking alone. A control antibody with the matched isotype to the one used to crosslink IgD was included to rule out any nonspecific effect of the IgD crosslinking antibody.

Figure 8:
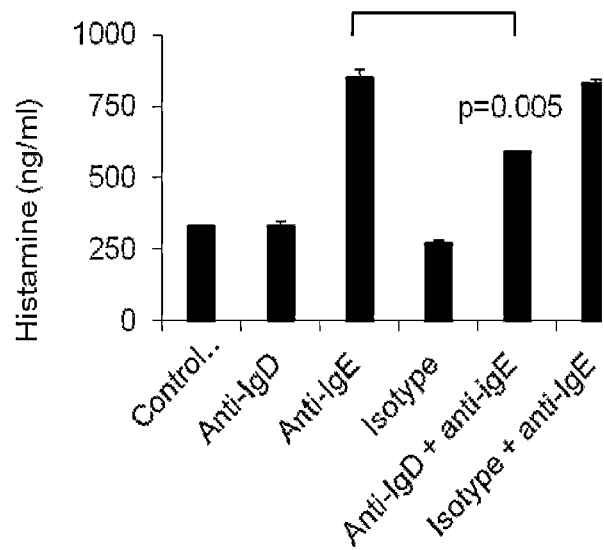
FIG. 8. Results from ELISA assays for histamine release (a) and flow cytometry of CD63, CD40L (b) and APRIL (c) of basophils exposed to microbeads alone (Control), microbead-bound monoclonal anti-IgD, microbead-bound monoclonal anti-IgE, microbead-bound isotype control antibody, microbeads-bound monoclonal anti-IgD and anti-IgE, or microbeads-bound isotype control antibody and monoclonal anti-IgE for 45 min (histamine release, CD63 expression) in the presence of IL-3, or 16 h (CD63, CD40L, APRIL expression) in the presence of IL-3 or TNF. Dead cells were excluded using 7-AAD staining.
Figure 8:
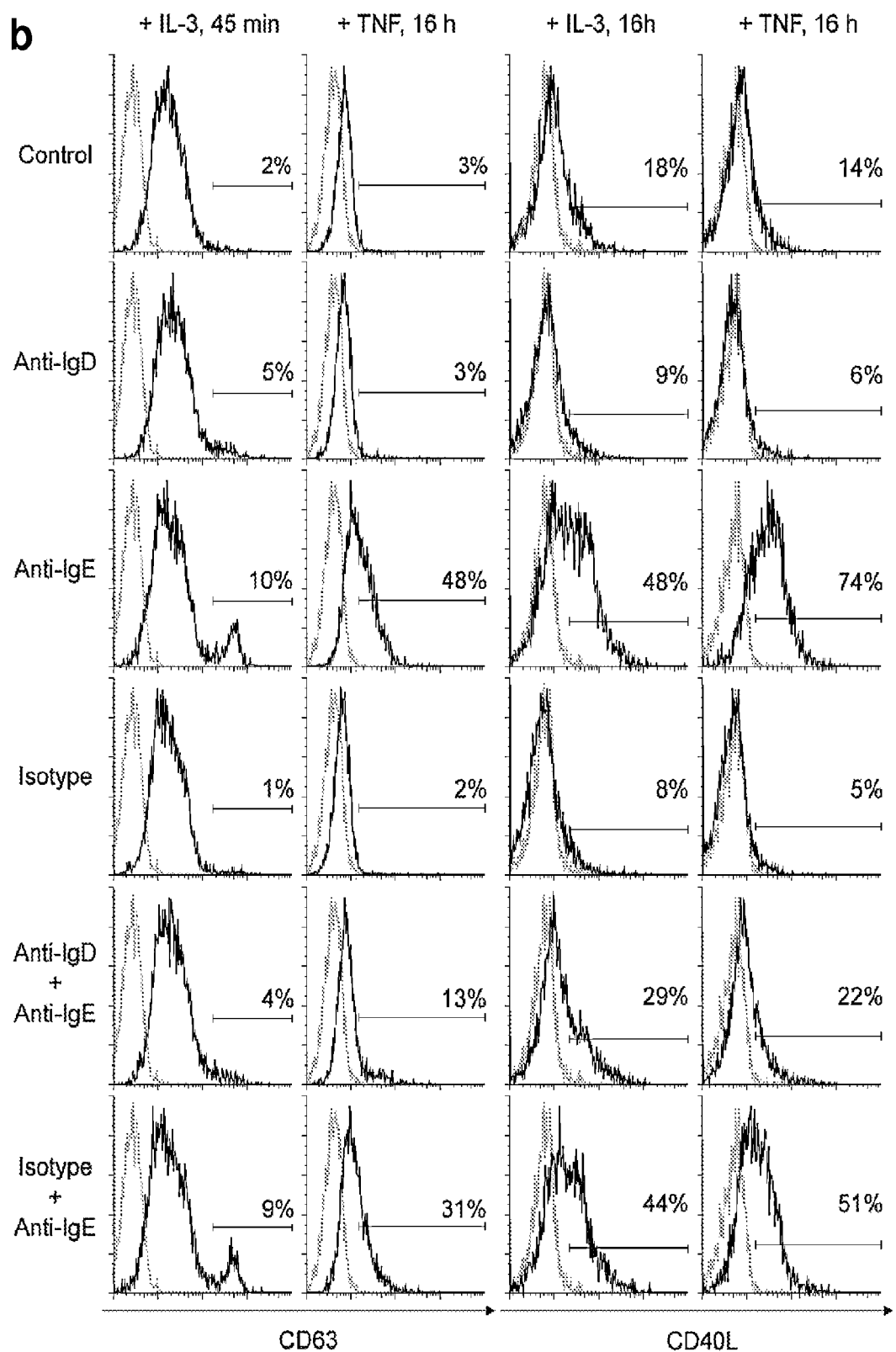

IgD co-crosslinking rendered basophils hypo-responsive to IgE-induced immediate degranulation, as evidenced by a reduced histamine release and diminished CD63 upregulation in response to IgE crosslinking in the presence of an IgD-crosslinking antibody but not the isotype-matched control antibody (FIGS. 8a-8b). IgD also inhibited IgE-induced CD40L upregulation in the presence of IL-3 or TNF (FIG. 8b).

Example 11

IgD Contains a Sequence Resembling the Consensus Ligand of Heparin

Figure 9:
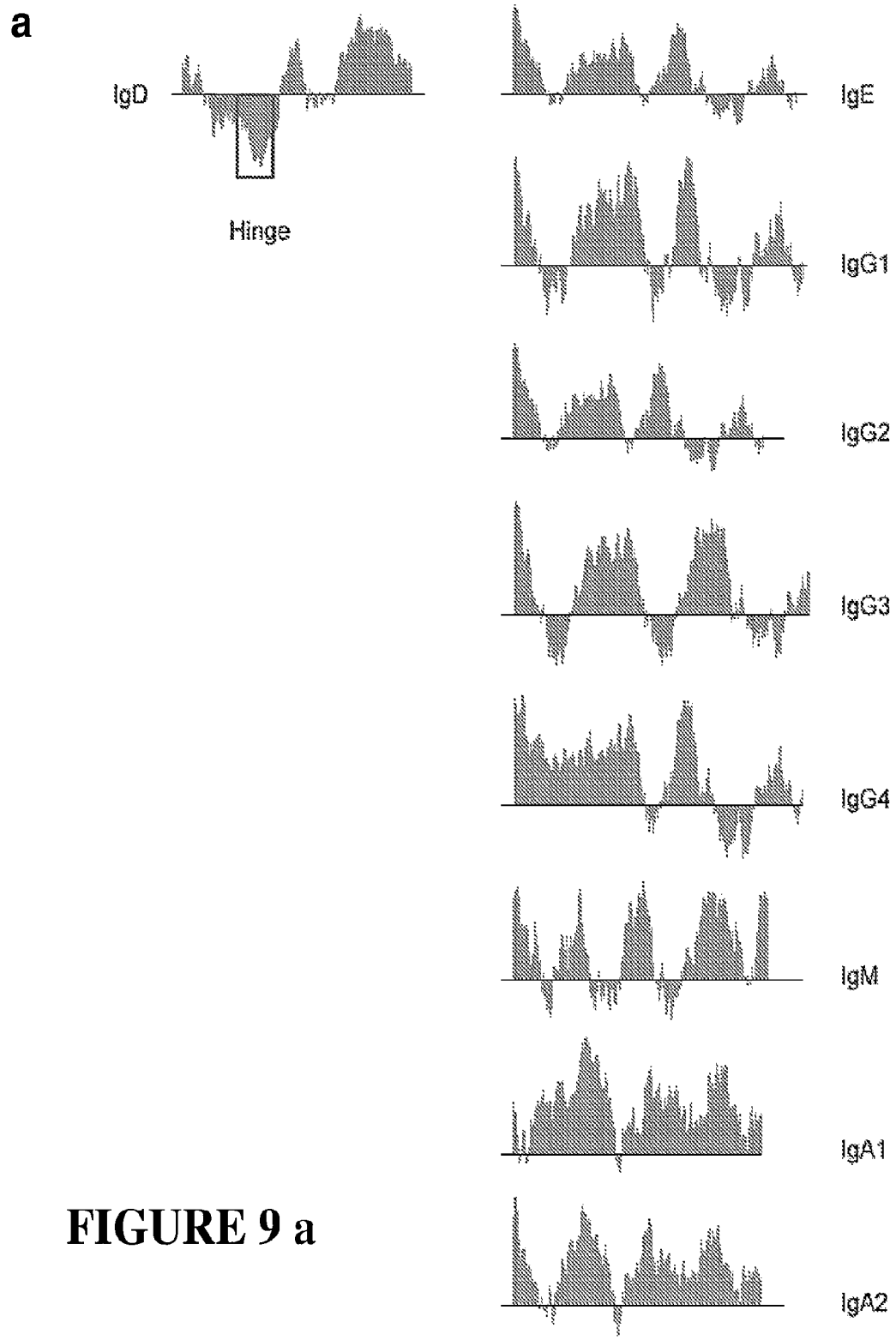
FIG. 9. Human IgD contains a sequence resembling that of consensus ligand of heparin. (a) Hydrophobicity indices of human Ig isotypes at pH 3.4 determined by HPLC in silica using the VectorNTI software. The region of high hydrophilicity in IgD is demarcated by a rectangle. Sequences of these proteins were downloaded from NCBI GenBank. GenBank IDs: IgD (P01880.2), IgE (P01854.1), IgG1 (AAH73782), IgG2 (AAH62335), IgG3 (AAH33178), IgG4 (AAh25985), IgM, (AAH89412), IgA1 (AAH87841), IgA2 (AAH73765). (b) Charged cluster analysis of human IgD performed using the SAPS (statistical analysis of protein sequences) program available online via the ISREC Software homepage. The charges of the amino acid residues of the δ heavy chain at physiological pH are indicated by either +, − or 0, meaning positively charged, negatively charged or neutral respectively. The charged cluster identified by the program is outlined in a rectangle. No positive cluster or negative cluster is identified. The analysis of the identified mix-charged cluster is shown below the whole sequence charge analysis. (c) Comparison of the charged hinge peptide of IgD with the proposed consensus α-helical ligand of heparin. Charges of the amino acid residues at physiological pH are indicated below the respectively amino acid. B, basic amino acid residue; X, hydropathic (either hydrophobic or hydrophilic) amino acid residue.

As demonstrated hereinabove, the binding of IgD to basophilic and mastocytoid cell lines was not inhibited by IgG, IgA or IgE, indicating that the receptor of IgD is distinct from those of IgG, IgA and IgE. The inventors also believe that IgD must possess some unique structural features different from other Ig classes that enable it to interact with basophils and MCs. The inventors compared the hydrophobicity of human IgD with other Ig isotype and found that the δ heavy chain has a region that is highly hydrophilic, which is not found in any other Ig isotypes (FIG. 9a). This region corresponds to the hinge region of IgD. Such a high degree of hydrophilicity results from the presence of abundant charged amino acid residues in this region, especially lysine (K), glutamate (E), serine (S) and threonine (T). A charge analysis was performed, which showed that this region has a mixed-charge cluster (the presence of at least 14 charged amino acid residues in a continuous stretch of 30 amino acid residues is qualified to be a mixed-charge cluster) (FIG. 9b). Further analysis of the charged cluster sequence revealed that it resembles the consensus α-helical ligand sequence of heparin (FIG. 9c), which sequence has been reported by Hileman et al. (*Bioessays* 20:156-67, 1998). The hinge region of IgD is known to adopt an α-helical conformation. Basophils and MCs are the major cell types that synthesize heparin, which forms the matrix of granules of these cells (Seldin et al. (*J Biol Chem* 260:11131-9, 1985); Hileman et al. (1998), supra; Wedemeyer et al. (*Curr Opin Immunol* 12:624-31, 2000)). Therefore, the inventors believe that heparin is a receptor of IgD on basophils and MCs.

Example 12

Materials and Methods

This Example describes the materials and methods used in the experiments described in Examples 1-11.

Fresh Cells.

Peripheral blood mononuclear cells from buffy coats of healthy subjects were purchased at the New York Blood Center. Additional mononuclear cells were isolated from the peripheral blood of patients with primary immunodeficiencies, mastocytosis or autoinflammatory syndromes. Tonsillar and pulmonary mononuclear cells were obtained from tissue specimens of patients undergoing resection of hypertrophic tonsils or lung neoplastic lesions at New York Presbyterian Hospital-Weill Cornell Medical Center. The Institutional Review Board of Weill Medical College of Cornell University approved the use of blood, tonsil and lung specimens for this study, and patients provided informed consent. IgD$^+$IgM$^+$ B cells and CD14$^+$ monocytes were magnetically sorted from peripheral blood and tonsillar mononuclear cells as reported (Litinskiy et al., *Nat. Immunol.* 3: 822-829, 2002). In the experiments involving induction of σδ-Sμ switch circles and loss of surface IgM, peripheral blood IgD$^+$IgM$^+$ B cells were depleted of antigen-experienced plasmablasts using CD27-targeting microbeads (Miltenyi Biotec). For morphological studies, IgD$^+$IgM$^+$ and IgD$^+$IgM$^-$ B cells were FACSorted from tonsillar mononuclear cells. Granulocytes were separated from peripheral blood mononuclear cells using Histopaque-1119 and Histopaque-1077 double gradients (Sigma). Untouched basophils were purified by negative selection from peripheral blood mononuclear cells using a Basophil Isolation Kit (Miltenyi Biotec). Mast cells were enriched from lung mononuclear cells using a biotin-conjugated AER-37 monoclonal antibody (mAb) to FcεRI (eBiosciennces) and anti-biotin microbeads (Miltenyi Biotec). Catfish peripheral blood lymphocytes were obtained and stained as reported (Bentgen et al., *J. Immunol.* 169: 2488-2497, 2002; Miller et al., *J. Immunol.* 152: 2180-2189, 1994). Catfish IgM and IgD were detected with 9E1 and 7D11 mAbs, respectively.

Cell Lines.

Primary epithelial cell lines from the oral cavity (Cambrex) were propagated as reported (Xu et al., *Nat. Immunol.* 8: 294-303, 2007). The T cell lines Jurkat and Molt-3, the B cell lines Reh, 2E2 and Ramos, the myeloid cell lines THP-1, U937 and HL60, and the pre-basophilic cell line KU812 were cultured in complete RPMI 1640 medium (Gibco). The T cell line HuT78 was cultured in complete Iscove's DMEM (Mediatech). The NK cell line NKL was cultured in complete RPMI 1640 medium further supplemented with 1% non-essential amino acids (Mediatech) and 200 U/ml IL-2. The NK cell line NK-92 was cultured in MEM-α medium with 2 mM glutamine, 1.5 mg/ml $NaHCO_3$, 0.1 mM β-mercaptoethanol, 0.02 mM folate, 0.2 mM inositol, 12.5% PBS and 12.5% horse serum. The mastocytoid cell line LAD2 (from A. Kirshenbaum and D. Metcalfe, National Institutes of Health) was cultured in serum-free Stem Pro-34 medium (Invitrogen) containing 100 ng/ml of stem cell factor (Peprotech). The mastocytoid cell line HMC-1 was cultured in Iscove's DMEM (Mediatech) with 10% FBS, 2 mM glutamine, 0.02% α-thioglycerol and antibiotics.

Tissues and Immunohistochemistry.

Frozen and paraffin-embedded tissue sections from tonsils, nasal cavities, intestine, liver, lymph nodes, bone marrow and spleen from healthy subjects or patients with primary immunodeficiencies or autoinflammatory syndromes were stored at −80° C. and room temperature, respectively. Sections were blocked with a saturating concentration of purified human IgG and stained for immunohistochemical analysis with various combinations of antibodies (Table 1) as described previously (Xu et al., *Nat. Immunol.* 8: 294-303, 2007). Primary antibodies with irrelevant binding activity and appropriate secondary reagents were utilized to test the specificity of tissue stainings as previously described (Xu et al., *Nat. Immunol.* 8: 294-303, 2007). The proportion of $IgD^+IgM^-$ plasmablasts in different organs was determined by sequentially staining tissue sections with a polyvalent goat polyclonal antibody (pAb) to human Igs (Cappel), an Alexa Fluor 647-conjugated secondary pAb to goat Igs, a fluorescein-conjugated goat $F(ab)_2$ pAb to human IgD (Southern Biotech), and a biotin-conjugated goat $F(ab')_2$ pAb to human IgM. Nuclei were visualized with DAPI, 4',6-diamidine-2'-phenylindole dihydrochloride (Boehringer Mannheim). The following formula was used: number of cytoplasmic $IgD^+IgM^-$ B cells/number of cytoplasmic $Ig^+$ B cells×100. Sections adjacent to those analyzed for IgM, IgD and total Ig were stained with 7G3 mAb to CD123. $IgD^+$ cells with no clear plasmacytoid morphology, but with granular cytoplasm, lobated nucleus and/or CD123 expression were scored as basophils and therefore excluded from the analysis. Follicular mantle $IgD^+IgM^-$ B cells were also excluded from the analysis. These B cells have bright IgD and dim IgM expression due to the higher stability and less rapid turnover of $VDJ-C_\delta$ transcripts compared to $VDJ-C_\mu$ transcripts (Preud'homme et al., *Mol. Immunol.* 37: 871-887, 2000). Pseudocolor images were composed using Metamorph 7.5 (Molecular Device) and edited using Photoshop CS2 (Adobe).

Patients.

HIGM patients had various TNFSF5, AICDA or TNFRSF5 gene mutations impairing the function of CD40L, AID and CD40, respectively (Cunningham-Rundles et al., *Nat. Rev. Immunol.* 5: 880-892, 2005). CVID patients had a heterozygous C104R mutation in the TNERSF13b gene. This mutation prevents the binding of BAFF and APRIL to TACI (Garibyan et al., *J. Clin. Invest.* 117: 1550-1557, 2007; Zhang et al., *J. Allergy Clin. Immunol.* 120: 1178-1185, 2007). The MWS patient had a heterozygous C1043T mutation in the NALP3/CIASPPYPAF1 gene. This mutation enhances the activity of cryopyrin, a key component of the inflammasome (Ryan et al., *Curr. Top. Microbiol. Immunol.* 321: 169-184, 2008). TRAPS patients had heterozygous G173A, G362A, or T123G mutations in the TNFRSF1A gene. These mutations prevent cleavage of the extracellular domain of TNF receptor type-1, thereby impairing feedback inhibition of the pro-inflammatory cytokine TNF-α by its soluble decoy receptor (Ryan et al., *Curr. Top. Microbiol. Immunol.* 321: 169-184, 2008). HIDS patients had a homozygous G1129A mutation or compound G632A and G1129A mutations of the MVK gene, which encodes mevalonate kinase. The mechanism by which these mutations cause inflammation remains unknown. PFAPA patients had no molecular diagnosis, except one, who was reported to have a heterozygous mutation in the MEFV gene encoding pyrin (also known as marenostrin), a negative regulator of the inflammasome (Ryan et al., *Curr. Top. Microbiol. Immunol.* 321: 169-184, 2008).

Bacteria.

*Moraxella catarrhalis* BAA-1425, *Haemophilus influenzae* type-a 9006, and *Haemophilus influenzae* type-b 9795 (American Type Cell Culture) were cultured according to the manufacturer's instructions.

Cultures and Reagents.

Cultures were performed in complete RPMI medium supplemented with 10% (volume/volume) bovine serum. Purified B cells were incubated with CD40L (Amgen), 500 ng/ml; BAFF (Alexis), 500 ng/ml; APRIL MegaLigand (Alexis), 500 ng/ml; IL-2 (Peprotech), 100 ng/ml; IL-10 (Peprotech), 50 ng/ml; IL-15 (Sigma), 50 ng/ml; and IL-21 (R&D Systems), 100 ng/ml. Cultures involving HIGM2 specimens were carried out with peripheral blood mononuclear cells instead of purified B cells due to the scarce amount of blood available. In these cultures, B cell activation was optimized by using 5 μg/ml goat $F(ab')_2$ pAb to human IgM (Southern Biotech). Purified basophils with Fc receptors already blocked during the purification step were incubated with or without 30 ng/ml of IL-3 (Peprotech) for 4 hours. These basophils were stimulated with 5 μl of anti-mouse IgG-coated microbeads (Miltenyi Biotec) mixed with one of the following antibodies: a control IgG2a mAb with irrelevant binding activity (Santa Cruz Biotechnology), 25 μg/ml; a mouse IgG2a 1A6-2 mAb to IgD (BD Biosciences), 25 μg/ml; or a mouse IgG2a G7-18 mAb to IgE (BD Biosciences), 2 μg/ml. Basophils stimulated with equal amounts of microbeads only were included as an additional control. Basophil-B cell co-cultures were set up by incubating $IgD^+IgM^+$ B cells with basophils activated as described above for 1 h (1:1 ratio). In these co-cultures, basophils were extensively washed to eliminate excess mAb to IgD or IgE before B cell addition.

Flow Cytometry.

Cells were incubated with an Fc blocking reagent (Miltenyi Biotec) or saturating concentrations of purified human IgG and stained on ice with appropriate combinations of pAbs and mAbs to various surface antigens (Table 1). 7-AAD was routinely used to exclude dead cells from the analysis. All gates and quadrants were drawn to give ≤1% total positive cells in the sample stained with control antibodies. Events were acquired on a FACS Calibur or BD LSR II (BD Biosciences) and analyzed by FlowJo (Tree Star). Tonsillar $IgD^+IgM^-$ plasmablasts were identified within an electronic gate containing $CD19^+$ mononuclear cells. These mononuclear cells also comprised follicular mantle $IgD^+IgM^+$ B cells, unswitched memory (or marginal zone-like) $IgD^{low}IgM^+$ B cells, and class-switched $IgD^-IgM^-$ memory B cells. Although visible by immunohistochemistry, $IgD^-IgM^+$ plasma cells were not always detected in the CD19 gate, probably because these IgM-forming cells are terminally differentiated and therefore express little or no CD19 and/or IgM on their surface. Often, also IgD⁻IgM⁺ germinal center B cells were not clearly detectable in the CD19 gate, possibly due to the very short life span (1-3 hours) of these cells after ex vivo isolation. Importantly, not all the IgD⁻IgM⁺ cells visualized in the germinal center corresponded to germinal center B cells. Indeed, many of these cells were follicular dendritic cells capturing IgM-containing immunocomplexes.

Enzyme-Linked Immunsorbent Assay (ELISA) and Cytometric Bead Array.

IgD (Bethyl Laboratories), histamine (Neogen Corporation), IL-1β, IL-4, IL-13, APRIL and TNF-α (Bender Medsystems) were measured by ELISAs as instructed by the manufacturer. IL-8 and CXCL10 were measured using Human Th1/Th2 Cytometric Bead Array (BD Biosciences). IgM, IgG, IgA and BAFF were detected by standard ELISAs as described (Litinskiy et al., *Nat. Immunol.* 3: 822-829, 2002), whereas IgE was measured by ELISA using a mAb to human IgE (G7-18, BD Biosciences) as capture antibody and a biotinylated mAb to human IgE (G7-26, BD Biosciences) as detection antibody. LL-37 was measured by ELISA using a mouse mAb to LL-37 (3D11, Hycult Biotechnology) as capture antibody and a rabbit pAb to LL-37 (PANATecs GmbH) as detection antibody, followed by a pAb to rabbit IgG conjugated to horseradish peroxidase (Santa Cruz Biotechnology). Human LL-37 peptide (PANATec GmbH) was used to generate a standard curve. Supernatants from basophil-containing cultures were centrifuged at 14,000 rpm for 20 min twice and adsorbed with mouse IgG before using them for ELISAs.

Genomic PCR, Southern Blotting, Cloning and Sequencing.

Switch circles are generally accepted as a marker of ongoing class switching, because they have a short half-life due to their rapid degradation by cellular nucleases (Muramatsu et al., Cell 102: 553-563, 2000; Chaudhuri et al., *Nat. Rev. Immunol.* 4: 541-552, 2004; Stavnezer, *Adv. Immunol.* 61:79-146, 1996). In addition, switch circles do not replicate with the class switched B cell and therefore become rapidly diluted after CSR takes place. For these reasons, it was decided to identify active CSR from IgM to IgD by PCR amplifying extrachromosomal σδ-Sμ reciprocal DNA recombination products instead of ligated chromosomal Sμ-σδ DNA products, which could be inflated by the proliferation of the class-switched B cells. Genomic DNA was extracted using the QIAamp DNA Mini Kit. σδ-Sμ switch circles were amplified from genomic DNA using elongase (Invitrogen) and a σδ sense primer 5'-TCATCATTGCCCAGATGCTAGGGCT-3' (SEQ ID NO: 5) coupled with an Sμ antisense primer 5'-TGAGTGCCCTCACTACITGCGTCCCG-3' (SEQ ID NO: 6) under the following conditions: initial denaturation for 30 sec at 94° C., followed by 35 cycles of denaturation for 30 sec at 94° C., annealing for 30 sec at 62° C., and extension for 7 min at 68° C., and a final extension for 15 min at 68° C. Products were resolved in a 1% agarose gel, transferred overnight onto nylon membranes, and hybridized with two ³²P-labeled probes specific to the 3' portion of Sμ and the 5' portion of σδ respectively. Hybridization products had multi-banded or smeary patterns on gel electrophoresis, because CSR randomly occurred in each B cell within large Sμ and σδ DNA regions. To further verify the specificity of PCR-amplified products, a second PCR was performed under the same conditions using the σδ sense primer 5'-TCATCATTGC-CCAGATGCTAGGGCT-3' (SEQ ID NO: 5) coupled with a nested Sμ primer 5'-CAGACTGTCATGGCTATCA GGGGTGGCGGGG-3' (SEQ ID NO: 7). PCR products longer than 1.5 kb were purified, ligated into pCR2.1 TOPO vectors, and transformed into *E. coli* using a TOPO TA cloning kit (Invitrogen). Plasmids in selected colonies were purified and sequenced. Sequences were aligned with human genomic DNA sequences to identify regions spanning both σδ and Sμ.

RT-PCR.

Active germline Cδ gene transcription and post-switch juxtaposition of chromosomal Iμ and Cδ exons were evaluated through the analysis of chimeric Iμ-Cδ transcripts in pre-switched and post-switched B cells, respectively. Total RNA was extracted using the QIAamp DNA Mini Kit and RNeasy Mini Kit (Qiagen) and cDNA was synthesized as previously described (Litinskiy et al., *Nat. Immunol.* 3, 822-829. (2002)). Iμ-Cδ transcripts were amplified from cDNA using Taq polymerase with an Iμ sense primer 5'-GTGAT-TAAGGAGAAACACTTTGAT-3' (SEQ ID NO: 8) and a Cδ antisense primer 5'-CTGGCCAGCGGAAGATCTCCT-TCTT-3' (SEQ ID NO: 9) under the following conditions: initial denaturation for 5 min at 94° C., followed by 25 cycles of denaturation for 1 min at 94° C., annealing for 1 min at 60° C. and extension for 1 min at 72° C., and a final extension for 7 min at 72° C. Bands were detected as described above, using 32P-labeled probes specific for Iμ and Cδ exons. RT-PCR products were cloned and sequenced to identify regions spanning both Iμ and Cδ.

QRT-PCR.

Total RNA was extracted from basophils using TRIzol (Invitrogen). cDNA synthesis and QRT-PCR were performed using various primer pairs (Table 2) as described (Xu et al., *Nat. Immunol.* 8: 294-303, 2007).

Calcium Flux Assay.

Basophils (2.5×10⁶) were resuspended in 1 ml of phosphate buffer solution containing 0.5% bovine serum albumine and 2 mM ethylenediaminetetraacetic acid. Cells were loaded with 5 μM Fura-3/AM (Sigma) for 30 min at 37° C. Excess Fura-3/AM was removed by washing cells twice in phosphate buffer solution. Cells were then stimulated as reported in the text. Intracellular $Ca^{2+}$ dynamics was monitored following the addition of stimulants in a plate reader with a 336 nm laser and a 495 nm filter. Readings were recorded every 40 seconds.

IgD Binding Assay.

Polyclonal or monoclonal IgD antibodies purified from the plasma of healthy individuals or multiple myeloma patients (Athens Research & Technology) were incubated at the indicated concentrations with various cell types (1×10⁵) for 20 min on ice. Binding assays were performed with a concentration of IgD within or below the physiological range of serum. IgD concentrations (15-300 μg/ml). Cells were then washed, stained with fluorescein-conjugated F(ab')₂ pAb to IgD (Southern Biotech), washed and analyzed by flow cytometry. This F(ab')₂ antibody had no cross-reactivity to other immunoglobulin classes and could not bind to Fc receptors due to the lack of its Fc portion. Cells stained with this pAb to IgD in the absence of purified IgD were used as background control. Alternatively, cells were stained with fluorescein-conjugated mouse IA6-2 or IgD26 mAbs to IgD.

Competitive IgD Binding Assays.

Monoclonal IgD purified from the plasma of a multiple myeloma patient was labeled with Alexa Fluor 488 using a Microscale Protein Labeling kit (Molecular Probes) and dialyzed in phosphate buffer solution overnight to remove excess fluorochrome. Freshly isolated peripheral blood basophils were stripped of bound endogenous IgD by incubation in an acidic sodium citrate buffer (40 mM sodium citrate, 140 mM NaCl, pH 3.0) for 3 min. Then, cells were quickly spun down to remove the acidic buffer and PBS was added to the cells to neutralize the pH. Basophils stripped of endogenous bound IgD were incubated with 0, 100 or 500 μg/ml unlabelled monoclonal IgD, followed by 40 μg/ml Alexa Fluor 488-labelled monoclonal IgD. After incubation, cells were washed and analyzed by flow cytometry. 7-AAD was used to exclude dead cells.

Statistical Analysis.

Values were expressed as mean±standard error of the mean (s.e.m.). Statistical significance was assessed by a one-tailed unpaired Student's t-test.

TABLE 1

Antibodies used for flow cytometry and immunofluorescence.

| Antigen [Epitope] | Label | Isotype | Clone (if monoclonal) | Manufacturer |
|---|---|---|---|---|
| AID | — | Rat IgG2b | EK2 5G9 | Cell Signaling |
| [C-20] | — | Goat IgG | — | Santa Cruz |
| [H-80] | — | Rabbit IgG | — | Santa Cruz |
| APRIL [AT125] | — | Rabbit IgG | — | Alexis |
| [N16] | — | Goat IgG | — | Santa Cruz |
|  | — | Rat IgG2a | Sacha-1 | Alexis |
| ED2 | — | Rabbit IgG | — | Prosci |
| BAFF (CD257) | PE | Mouse IgG1 | 1D6 | eBioscience |
|  | Biotin | Mouse IgG1 | 1D6 | eBioscience |
|  | — | Mouse IgG2b | 137314 | R&D Systems |
|  | — | Rabbit IgG | — | Upstate |
| BAFF-R (CD268) | PE | Mouse IgG1 | 11C1 | BD Biosciences |
| BCMA [N-16] | — | Goat IgG | — | Santa Cruz |
| Blimp-1 | — | Mouse IgG1 | 3H2-E8 | Novus Biologicals |
| CD3 | FITC | Mouse IgG1 | UCHT1 | Ancell |
|  | Biotin | Mouse IgG1 | UCHT1 | BD Biosciences |
| CD4 | FITC | Mouse IgG2b | M-T441 | Ancell |
|  | Biotin | Mouse IgG1 | SK3 | BD Biosciences |
| CD5 | PE | Mouse IgG1 | UCHT2 | BD Biosciences |
| CD8 | PE | Mouse IgG2a | UCHT4 | Sigma |
| CD10 | PE | Mouse IgG1 | ALB1 | Immunotech |
| CD11b | PE | Mouse IgG2a | D12 | BD Biosciences |
| CD11c | PE | Mouse IgG1 | B-ly6 | BD Biosciences |
| CD14 | PE | Mouse IgG2a | UCHM-1 | Sigma |
|  | Biotin | Mouse IgG2a | UCHM-1 | Southern Biotech |
| CD15 | FITC | Mouse IgM | 28 | Southern Biotech |
| CD16 | Biotin | Mouse IgG1 | 3G8 | BD Biosciences |
| CD19 | FITC | Mouse IgG1 | SJ25-C1 | Southern Biotech |
|  | PE | Mouse IgG1 | 4G7 | BD Biosciences |
|  | APC | Mouse IgG1 | H1B19 | BD Biosciences |
|  | Biotin | Mouse IgG1 | H1B19 | BD Biosciences |
| CD20 | FITC | Mouse IgG1 | L27 | BD Biosciences |
| CD21 | PE | Mouse IgG1 | B-ly4 | BD Biosciences |
| CD22 | — | Mouse IgG1 | FPC1 | Novocastra |
| CD23 | FITC | Mouse IgG1 | 9P25 | Immunotech |
| CD24 | PE | Mouse IgG2a | ML5 | BD Biosciences |
| CD27 | FITC | Mouse IgG1 | M-T271 | BD Biosciences |
|  | PE | Mouse IgG1 | M-T271 | Ancell |
|  | APC | Mouse IgG1 | O323 | eBioscience |
| CD31 | FITC | Mouse IgG1 | WM-59 | eBioscience |
| CD38 | PE | Mouse IgG1 | HIT2 | BD Biosciences |
|  | APC | Mouse IgG2b | IB6 | Miltenyi Biotech |
| CD40 | FITC | Mouse IgG1 | BE-1 | Ancell |
| CD56 | FITC | Mouse IgG2b | NCAM16.2 | BD Biosciences |
| CD63 | FITC | Mouse IgG1 | AHN16.1/46-4-5 | Ancell |
|  | Biotin | Mouse IgG1 | AHN16.1/46-4-5 | Ancell |
| CD83 | FITC | Mouse IgG1 | HB15e | Ancell |
| CD117 | PE | Mouse IgG1 | 104D2 | BD Biosciences |
|  | — | Rabbit IgG | — | DAKO |
| CD123 | PE | Mouse IgG2a | 7G3 | BD Biosciences |
|  | APC | Mouse IgG1 | 6H6 | eBioscience |
| CD124 | Biotin | Mouse IgG1 | hIL4R-M57 | BD Biosciences |
| CD138 | PE | Mouse IgG1 | Mi15 | BD Biosciences |
| CD154 (CD40L) | PE | Mouse IgG1 | 24-31 | Ancell |
| FcεRIα | Biotin | Mouse IgG2b | AER-37 | eBioscience |
| HLA-DR | FITC | Mouse IgG2a | L243 | BD Biosciences |
|  | PE | Mouse IgG2a | L243 | BD Biosciences |
| IgA | FITC | Goat IgG | — | Sigma Aldrich |
|  | PE | Goat IgG F(ab')$_2$ | — | Southern Biotech |
|  | Biotin | Goat IgG F(ab')$_2$ | — | Southern Biotech |
| IgD | FITC | Goat IgG F(ab')$_2$ | — | Southern Biotech |
|  | PE | Mouse IgG2a | IADB6 | Southern Biotech |
|  | Biotin | Goat IgG F(ab')$_2$ | — | Southern Biotech |
|  | — | Mouse IgG2a | IA6-2 | BD Biosciences |

TABLE 1-continued

Antobodies used for flow cytometry and immunofluorescence.

| Antigen [Epitope] | Label | Isotype | Clone (if monoclonal) | Manufacturer |
|---|---|---|---|---|
| IgE | FITC | Goat IgG | — | CAPPEL |
| | Biotin | Mouse IgG2a | G7-26 | BD Biosciences |
| IgG | FITC | Goat IgG | — | Sigma Aldrich |
| | PE | Goat IgG | — | Sigma Aldrich |
| | Biotin | Goat IgG F(ab')$_2$ | — | Southern Biotech |
| IgM | FITC | Goat IgG F(ab')$_2$ | — | Biosource |
| | PE | Mouse IgG1 | SA-DA4 | Southern Biotech |
| | Biotin | Goat IgG F(ab')$_2$ | — | Southern Biotech |
| | — | Goat IgG F(ab')$_2$ | — | Caltag |
| Igκ | PE | Mouse IgG1 | G20-193 | BD Pharmingen |
| | — | Goat IgG F(ab')$_2$ | — | Caltag |
| Igλ | PE | Mouse IgG1 | 1-155-2 | BD Pharmingen |
| | — | Goat IgG F(ab')$_2$ | — | Caltag |
| Ki67 | — | Mouse IgG1 | MIB-1 | DAKO |
| LL-37 | — | Rabbit IgG | — | PANATecs GmbH |
| MHC-I | PE | Mouse IgG2a | 3F10 | Ancell |
| MHC-II | PE | Mouse IgG1 | TDR31.3 | Ancell |
| Pax5 (BSAP) | — | Mouse IgG2a | A-11 | Santa Cruz |
| RAG2 [C-19] | — | Goat IgG | — | Santa Cruz |
| TACI | PE | Mouse IgG1 | 165604 | R&D Systems |
| | Biotin | Mouse IgG2a | 11H3 | eBioscience |
| [C-20] | — | Goat IgG | — | Santa Cruz |
| Tryptase | — | Mouse IgG1 | AA1 | DAKO |
| ZO1 | — | Rabbit IgG | — | Zymed |

TABLE 2

Primers used for QRT-PCR.

| Target Gene | | Primer sequence | SEQ ID | $T_m$ Used (° C.) |
|---|---|---|---|---|
| ACTB | S | GGATGCAGAAGGAGATCACT | 10 | 58 |
| | AS | CGATCCACACGGAGTACTTG | 11 | |
| CAMP | S | GTCACCAGAGGATTGTGACTTCAA | 12 | 58 |
| | AS | TTGAGGGTCACTGTCCCCATA | 13 | |
| CRP | S | ATACACTGTGGGGGCAGAAG | 14 | 58 |
| | AS | CCGCCAAGATAGATGGTGTT | 15 | |
| CXCL10 | S | TGAGCCTACAGCAGAGGAA | 16 | 62 |
| | AS | TACTCCTTGAATGCCACTTAGA | 17 | |
| DEFB103A | S | TATCTTCTGTTTGCTTTGCTCTTC | 18 | 58 |
| | AS | CCTCTGACTCTGCAATAATATTTCTGTAA | 19 | |
| IL4 | S | ACTTTGAACAGCCTCACAGAG | 20 | 58 |
| | AS | TTGGAGGCAGCAAAGATGTC | 21 | |
| IL8 | S | CCAAACCTTTCCACCC | 22 | 53 |
| | AS | ACTTCTCCACAACCCT | 23 | |
| IL13 | S | TGAGGAGCTGGTCAACATCA | 24 | 58 |
| | AS | CAGGTTGATGCTCCATACCAT | 25 | |
| PTX3 | S | GGGACAAGCTCTTCATCATGCT | 26 | 58 |
| | AS | GTCGTCCGTGGCTTGCA | 27 | |
| SPAG11A/F | S | CTGTTTCCAGGATCGTCTCA | 28 | 58 |
| | AS | GAGATGTGCACTTGGTAAGG | 29 | |
| SPAG11D/G | S | CTGTTTCCAGGATCGTCTCA | 30 | 58 |
| | AS | GGAACATCCCCTTGGTAAGG | 31 | |
| TNFSF13B | S | ACCGCGGGACTGAAAATCT | 32 | 60 |
| | AS | CACGCTTATTTCTGCTGTTCTGA | 33 | |

Example 13

Summary of the Experimental Results

Human B cells from the upper respiratory mucosa were found to actively class switch from $S_\mu$ to $\sigma_\delta$, thereby generating local and circulating IgD antibodies highly reactive to respiratory bacteria. Circulating IgD was found to bind to basophils through a calcium-mobilizing receptor that activated antimicrobial, opsonizing, pro-inflammatory and B cell-stimulating programs upon cross-linking. Both IgD class-switched B cells and IgD-armed basophils were dysregulated in patients with autoinflammatory syndromes and periodic fever, indicating that IgD orchestrates an ancestral surveillance system at the interface between immunity and inflammation.

A large fraction of IgD$^+$IgM$^-$ plasmablasts were found in the upper respiratory mucosa. These plasmablasts originated in situ from an active process of S$\mu$-to-$\sigma\delta$ CSR that involved germline I$\mu$-C$\delta$ transcription, required AID expression, and occurred through either a TD follicular pathway involving engagement of CD40 on B cells by CD40L on T cells, or a TI extrafollicular pathway involving engagement of TACI on B cells by BAFF or APRIL from innate immune cells, possibly including epithelial and dendritic cells.

IgD$^+$IgM$^-$ plasmablasts in the peripheral blood are likely in transit from inductive sites in the upper respiratory mucosa to distant mammary, salivary, lacrimal, respiratory, tubal and auditive sites. IgD released by stimulated IgD$^+$IgM$^-$ B cells showed strong binding activity against respiratory bacteria and their products, including *Moraxella catarrhalis, Haemophilus influenzae*, LPS, CPS and MID.

Abundant IgD were detected herein on basophils, but not on other leukocytes, except B cells. In the presence of IgD cross-linking, basophils acquired the ability to inhibit the growth of respiratory bacteria, presumably through the induction of β-defensin 3, SPAG11 isoforms, PTX3, CRP and cathelicidins. These antimicrobial and opsonizing factors also have immunostimulating and alarm-inducing activity as reported by others (Yamaguchi et al., *J. Immunol.* 169: 2516-2523, 2002; Oppenheim et al., *Curr. Opin. Immunol.* 17: 359-365, 2005; Garlanda et al., *Annu. Rev. Immunol.* 23: 337-366, 2005). Thus, IgD-armed basophils are believed to function as circulating sentinels capable of triggering quick innate and adaptive immune responses upon sensing pathogens from the upper respiratory tract.

Basophils were found to up-regulate the production of IL-4, IL-13, BAFF and APRIL upon IgD cross-linking in vitro. This effect correlated with the acquisition of B cell-licensing functions, including the capability to elicit IgM secretion as well as IgG and IgA class switching. It is likely that basophils respond to IgD-reactive pathogens by eliciting not only innate, but also adaptive immune responses. Such responses would take place in both systemic and mucosal districts.

In addition to basophils, IgD was found bound to mast cells through an IL-4-inducible calcium-fluxing receptor distinct from IgG, IgA and IgE receptors. Indeed, basophil-like and mast cell-like lines pre-treated with IgG, IgA and IgE retained IgD binding activity. A minimal but reproducible inhibition was induced by IgA, the only antibody isotype together with IgD exhibiting $C_H$ region-associated O-linked carbohydrates (Gala et al., *J. Biol. Chem.* 277: 29005-29011, 2002). Basophils increased IgD binding in response to IL-3, a mast cell-derived cytokine that enhances basophil activation and recruitment to lymphoid and mucosal effector sites. Since IL-3 also enhanced basophil activation by IgD, basophils and mast cells may form an IgD-mediated IL-3-dependent axis for the amplification of both systemic and mucosal immune responses.

The interaction of IgD with basophils and mast cells was sensitive to the proteolytic activity of trypsin and papain, but not to that of pepsin. IgD clearly stimulated basophils through a pathway distinct from that induced by IgE. In spite of eliciting IgE-like intracellular calcium fluxes, IgD cross-linking did not induce degranulation and histamine release. Furthermore, IgD was less effective than IgE cross-linking in up-regulating surface CD40L, a powerful class switch-inducing factor. Conversely, IgD was generally more effective than IgE cross-linking in inducing antimicrobial, immunostimulating and pro-inflammatory factors such as IL-1β, TNF-α, IL-8 and CXCL10.

The pro-inflammatory function of IgD was further supported by the analysis of autoinflammatory syndromes, a group of disorders characterized by periodic attacks of fever and inflammation as well as exaggerated IL-1β and IgD production. More class-switched IgD$^+$IgM$^-$ plasmablasts and more mucosal IgD-armed basophils were found in patients with HIDS, TRAPS, MWS or PFAPA syndrome.

In summary, human B cells may produce IgD to instruct basophils as to the antigenic composition of the upper respiratory tract. This evolutionarily conserved immune surveillance system would not only monitor systemic invasion by airborne pathogens, but also regulate B cell homeostasis, antibody production and inflammation.

What is claimed is:

1. A method of attenuating an IgE-mediated response from basophils in a subject having an IgE-mediated disorder, comprising administering to said subject an unconjugated anti-IgD antibody that causes cross-linking of IgD pre-bound to the surface of said basophils to attenuate said IgE-mediated response from basophils thereby treating said IgE-mediated disorder.

2. The method of claim 1, wherein said IgE-mediated response is histamine release.

3. The method of claim 1, wherein said unconjugated anti-IgD antibody is a monoclonal antibody.

4. The method of claim 1, wherein said unconjugated anti-IgD antibody is a polyclonal antibody.

5. The method of claim 1, wherein said IgE-mediated disorder is selected from the group consisting of asthma, atopic dermatitis, allergic rhinitis, allergic conjunctivitis, eczema, urticaria, food allergy and seasonal allergy.

6. The method of claim 1, wherein said unconjugated anti-IgD antibody is administered by injections, inhalations, ingestions or implantations.

7. The method of claim 1, wherein said unconjugated anti-IgD antibody is a deimmunized antibody.

8. The method of claim 1, wherein said unconjugated anti-IgD antibody is a multivalent antibody fragment.

* * * * *

UNITED STATES PATENT AND TRADEMARK OFFICE
CERTIFICATE OF CORRECTION

| | | |
|---|---|---|
| PATENT NO. | : 8,828,394 B2 | Page 1 of 1 |
| APPLICATION NO. | : 13/260008 | |
| DATED | : September 9, 2014 | |
| INVENTOR(S) | : Andrea Cerutti et al. | |

It is certified that error appears in the above-identified patent and that said Letters Patent is hereby corrected as shown below:

In the Specification

It Should Read:

Column 1, line 16: R01AI057653 supplement, R01AI074378 and T32AI07621. The Government has certain rights in this invention.

Signed and Sealed this
Twelfth Day of May, 2015

Michelle K. Lee
*Director of the United States Patent and Trademark Office*

SEQUENCE LISTING

```
<160> NUMBER OF SEQ ID NOS: 33

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Lys Lys Lys Glu Lys Glu Lys Glu Glu Gln Glu Glu Arg Glu Thr Lys
1               5                   10                  15

Thr Pro Glu Cys
            20
```

```
<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Glu Lys Lys Lys Glu Lys Glu Lys Glu Gln Glu Glu Arg Glu Thr
1               5                   10                  15

Lys Thr Pro Glu Cys
            20

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a hydropathic amino acid
<220> FEATURE:
<221> NAME/KEY: MISC_FEATURE
<222> LOCATION: (2)..(4)
<223> OTHER INFORMATION: Xaa is a basic amino acid
<220> FEATURE:
<221> NAME/KEY: MISC_FEATURE
<222> LOCATION: (5)..(5)
<223> OTHER INFORMATION: Xaa is a hydropathic amino acid
<220> FEATURE:
<221> NAME/KEY: MISC_FEATURE
<222> LOCATION: (6)..(6)
<223> OTHER INFORMATION: Xaa is a basic amino acid
<220> FEATURE:
<221> NAME/KEY: MISC_FEATURE
<222> LOCATION: (7)..(7)
<223> OTHER INFORMATION: Xaa is a hydropathic amino acid

<400> SEQUENCE: 3

Xaa Xaa Xaa Xaa Xaa Xaa Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is a hydropathic amino acid
<220> FEATURE:
<221> NAME/KEY: MISC_FEATURE
<222> LOCATION: (2)..(4)
<223> OTHER INFORMATION: Asx is a basic amino acid
<220> FEATURE:
<221> NAME/KEY: MISC_FEATURE
<222> LOCATION: (5)..(6)
<223> OTHER INFORMATION: Xaa is a hydropathic amino acid
<220> FEATURE:
<221> NAME/KEY: MISC_FEATURE
<222> LOCATION: (7)..(7)
<223> OTHER INFORMATION: Asx is a basic amino acid
<220> FEATURE:
<221> NAME/KEY: MISC_FEATURE
<222> LOCATION: (8)..(8)
<223> OTHER INFORMATION: Xaa is a hydropathic amino acid

<400> SEQUENCE: 4

Xaa Asx Asx Asx Xaa Xaa Asx Xaa
```

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 5
tcatcattgc ccagatgcta gggct                                    25

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 6
tgagtgccct cactacttgc gtcccg                                   26

<210> SEQ ID NO 7
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 7
cagactgtca tggctatcag gggtggcggg g                             31

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 8
gtgattaagg agaaacactt tgat                                     24

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 9
ctggccagcg gaagatctcc ttctt                                    25

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 10
ggatgcagaa ggagatcact                                          20

<210> SEQ ID NO 11
<211> LENGTH: 20
<212> TYPE: DNA
<213> ORGANISM: Artificial Sequence

```
<220> FEATURE:
<223> OTHER INFORMATION: Synthetic oligonucleotide primer

<400> SEQUENCE: 11
cgatccacac ggagtacttg                                              20

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 12
gtcaccagag gattgtgact tcaa                                         24

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 13
ttgagggtca ctgtccccat a                                            21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
atacactgtg ggggcagaag                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 15
ccgccaagat agatggtgtt                                              20

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 16
tgagcctaca gcagaggaa                                               19

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 17
tactccttga atgccactta ga                                           22
```

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 18
tatcttctgt ttgctttgct cttc                                          24

<210> SEQ ID NO 19
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 19
cctctgactc tgcaataata tttctgtaa                                     29

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 20
actttgaaca gcctcacaga g                                             21

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 21
ttggaggcag caaagatgtc                                               20

<210> SEQ ID NO 22
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 22
ccaaaccttt ccaccc                                                   16

<210> SEQ ID NO 23
<211> LENGTH: 16
<212> TYPE: DNA
<213> ORGANISM: Artificial Sequence
<220> FEATURE:
<223> OTHER INFORMATION: Synthetic oligonucleotide primer

<400> SEQUENCE: 23
acttctccac aaccct                                                   16

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 24
tgaggagctg gtcaacatca                                               20

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 25
caggttgatg ctccatacca t                                             21

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 26
gggacaagct gttcatcatg ct                                            22

<210> SEQ ID NO 27
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 27
gtcgtccgtg gcttgca                                                  17

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 28
ctgtttccag gatcgtctca                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 29
gagatgtgca cttggtaagg                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 30
ctgtttccag gatcgtctca                                               20

<210> SEQ ID NO 31

```
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 31
ggaacatccc cttggtaagg                                            20

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 32
accgcgggac tgaaaatct                                             19

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 33
cacgcttatt tctgctgttc tga                                        23
```